(12) United States Patent
Abe et al.

(10) Patent No.: US 8,709,816 B2
(45) Date of Patent: Apr. 29, 2014

(54) HUMAN RENAL DISEASE MARKER SUBSTANCE

(75) Inventors: Takaaki Abe, Miyagi (JP); Tomoyoshi Soga, Yamagata (JP)

(73) Assignees: Tohoku University, Miyagi (JP); Keio University, Tokyo (JP)

( * ) Notice: Subject to any disclaimer, the term of this patent is extended or adjusted under 35 U.S.C. 154(b) by 0 days.

(21) Appl. No.: 13/393,091

(22) PCT Filed: Sep. 3, 2010

(86) PCT No.: PCT/JP2010/005434
§ 371 (c)(1),
(2), (4) Date: Apr. 12, 2012

(87) PCT Pub. No.: WO2011/027573
PCT Pub. Date: Mar. 10, 2011

(65) Prior Publication Data
US 2012/0193527 A1 Aug. 2, 2012

(30) Foreign Application Priority Data
Sep. 4, 2009 (JP) ................................. 2009-205033

(51) Int. Cl.
*G01N 33/48* (2006.01)
*G01N 33/00* (2006.01)

(52) U.S. Cl.
USPC ............................................ 436/63; 436/131

(58) Field of Classification Search
USPC .................................................... 436/63, 131
See application file for complete search history.

(56) References Cited

FOREIGN PATENT DOCUMENTS

| JP | 2000-146980 | 5/2000 |
| JP | 2007-519394 | 7/2007 |
| JP | 2008-538173 | 10/2008 |

OTHER PUBLICATIONS

Bylund et al. Analysis of Low Molecular Mass Organic Acids in Natural Waters by Ion Exclusion Chromatography Tandem Mass Spectrometry; Journal of Chromatography A, vol. 1176 (2007) pp. 89-93.*
Lewis et al. Metabolite Profiling of Blood From Individuals Undergoing Planned Myocardial Infarction Reveals Early Markers of Myocardial Injury; The Journal of Clinical Investigation, vol. 118, No. 10 (2008) pp. 3503-3512.*

(Continued)

*Primary Examiner* — Susan Hanley
*Assistant Examiner* — Paul Martin
(74) *Attorney, Agent, or Firm* — Kenneth H. Sonnenfeld; Margaret B. Brivanlou; King & Spalding LLP

(57) ABSTRACT

The present invention relates to a method for diagnosing, and treating renal disease in a patient by having a test performed for detecting or quantifying one or more renal disease markers present in a test blood sample from the patient; and administering treatment to improve renal function. In particular embodiments, the test performed quantifies cis-aconitate, and the patient is identified as having the renal disease when a concentration of cis-aconitate present in the patient's test blood sample is higher than that of a control. Methods of the present invention can allow diagnosis and treatment of patients with early stage renal disease, such as early stage renal failure. Another aspect of the present invention relates to methods for screening for a prophylactic/therapeutic agent for treating renal disease using one or more renal disease markers.

6 Claims, 49 Drawing Sheets

(56) References Cited

OTHER PUBLICATIONS

Haas et al. High-Performance Liquid Chromatographic Measurement of Selected Blood Citric Acid Cycle Intermediates; Journal of Chromatography, vol. 425 (1988) pp. 47-57.*

Huang et al. Metabonomic Profiling of Plasma Intermediates in Wistar Rats to Study the Effect of Aging by Means of GC/TOFMS-Based Techniques; Acta Pharmaceutica Sinica, vol. 44, No. 10 (2009) pp. 1095-1101.*

Mao et al. Metabonomic Analysis of Hapatitis B Virus-Induced Liver Failure: Identification of Potential Diagnostic Biomarkers by Fuzzy Support Vector Machine; J. Zhejiang Sci. B, vol. 9, No. 6 (2008) pp. 474-481.*

Alberghini et al., "Loss of the von Hippel Lindau Tumor Suppressor Disrupts Iron Homeostasis in Renal Carcinoma Cells," *J. Biol. Chem.*, 280(34), pp. 30120-30128, 2005.

International Search Report for PCT/JP2010/005434, dated Oct. 12, 2010, 4 pages.

* cited by examiner

Figure 1

BACKGROUND OF PATIENTS WITH CKD

| | | |
|---|---|---|
| AGE | 62.8 ± 14.6 (27–84) | |
| SEX (MALE/FEMALE) | 26/25 | |
| CREATININE | 2.64 ± 1.60 (0.8–7.4) | |
| eGFR | 24.4 ± 13.9(5.9–57.0) | |
| PRIMARY DISEASE of CKD | Alport syndrome | 1 (2.4%) |
| | analgesic-induced nephropathy | 1 (2.4%) |
| | ANCA related nephropathy | 1 (2.4%) |
| | aortitis syndrome | 1 (2.4%) |
| | bilateral renal infarction | 1 (2.4%) |
| | DM nephropathy | 8 (19.5%) |
| | FSGS | 3 (7.3%) |
| | glomerulosclerosis | 4 (9.7%) |
| | hydronephrosis | 1 (2.4%) |
| | IgA nephropathy | 9 (21.9%) |
| | lipoprotein glomerulopathy | 1 (2.4%) |
| | lupus nephropathy | 2 (4.8%) |
| | membrane proliferative glomerulonephrtis | 1 (2.4%) |
| | membranous nephropathy | 2 (4.8%) |
| | polycystic kidney | 1 (2.4%) |
| | primary renal disease | 2 (4.8%) |
| | renal tubercurosis | 1 (2.4%) |
| | sarcoidosis | 1 (2.4%) |
| UNDERLYING DISEASE | cardiovascular disease | 10 (24.3%) |
| | diabetes mellitus | 12 (29.2%) |
| | hypertension | 40 (97.5%) |
| | smoking | 11 (26.8%) |
| ORAL DRUG | allopurinol | 12 (29.2%) |
| | ARB | 30 (73.1%) |
| | AST-120 | 5 (12.1%) |
| | erythropoietin | 6 (14.6%) |
| | statin | 8 (19.5%) |

Figure 2

Cation

SUBSTANCES THAT ACCUMULATE WITH REDUCTION IN eGFR

| Compound | Spearman correlation coefficients | p value |
|---|---|---|
| Creatinine | -0.965 | <0.001 |
| SDMA | -0.948 | <0.001 |
| Guanidinosuccinate | -0.893 | <0.001 |
| Citrulline | -0.801 | <0.001 |
| 1-Methyladenosine | -0.772 | <0.001 |
| N-Acetylglucosamine | -0.751 | <0.001 |
| gamma-Butyrobetaine | -0.734 | <0.001 |
| Ophthalmate | -0.687 | <0.001 |
| 3-Methylhistidin | -0.669 | <0.001 |
| Hydroxyproline | -0.666 | <0.001 |
| Trimethylamine N-oxide | -0.665 | <0.001 |
| Allantoin | -0.653 | <0.001 |
| ADMA | -0.614 | <0.001 |
| Nepsilon-Acetyllysine | -0.602 | <0.001 |
| Kynurenine | -0.579 | <0.001 |
| Cytosine | -0.570 | <0.001 |
| Indole-3-acetate | -0.475 | 0.002 |
| Hypotaurine | -0.447 | 0.004 |
| N,N-Dimethylglycine | -0.428 | 0.006 |
| 7-Methylguanine | -0.406 | 0.010 |
| Methionine sulfoxide | -0.405 | 0.010 |
| Asn | -0.337 | 0.033 |
| Cysteine-glutathione disulphide | -0.279 | 0.077 |
| Gln | -0.273 | 0.083 |
| Arg | -0.271 | 0.087 |
| His | -0.267 | 0.091 |
| Ethanolamine phosphate | -0.261 | 0.098 |
| Gly | -0.258 | 0.102 |
| Piperazine | -0.253 | 0.110 |
| beta-Ala | -0.243 | 0.124 |
| Ornithine | -0.192 | 0.244 |
| Homoarginine ; N6-N6-N6-Trimethyllysine | -0.183 | 0.248 |
| Sarcosine | -0.182 | 0.250 |
| Pipecolate | -0.122 | 0.439 |
| o-Acetylcarnitine | -0.116 | 0.453 |
| Pro | -0.113 | 0.474 |
| Butamate | -0.108 | 0.491 |
| 5-Methyltetrahydrofolate | -0.088 | 0.576 |
| Ala | -0.070 | 0.656 |
| 5-Oxoproline | -0.032 | 0.837 |
| Taurine | -0.024 | 0.879 |
| Ser | -0.0003 | 0.998 |

SUBSTANCES THAT DECREASE WITH REDUCTION IN eGFR

| Compound | Spearman correlation coefficients | p value |
|---|---|---|
| Trp | 0.658 | <0.001 |
| Val | 0.478 | 0.002 |
| Tyr | 0.453 | 0.004 |
| 2-Aminobutyrate | 0.453 | 0.004 |
| Guanidoacetate | 0.441 | 0.005 |
| Glu | 0.422 | 0.007 |
| Leu | 0.386 | 0.014 |
| Asp | 0.262 | 0.097 |
| Hypoxanthine | 0.259 | 0.101 |
| Ile | 0.225 | 0.153 |
| Lys | 0.218 | 0.166 |
| Glycerophosphorylcholine | 0.211 | 0.182 |
| Guanosine | 0.207 | 0.190 |
| 1-Methyl-2-pyrrolidone | 0.207 | 0.190 |
| Carnitine | 0.202 | 0.201 |
| Inosine | 0.193 | 0.223 |
| Urocanate | 0.181 | 0.251 |
| 1-Methylnicotinamide | 0.166 | 0.294 |
| Thr | 0.152 | 0.336 |
| Met | 0.121 | 0.444 |
| Betaine | 0.098 | 0.535 |
| Creatine | 0.084 | 0.593 |
| Phe | 0.056 | 0.712 |
| alpha-Aminoadipate | 0.045 | 0.775 |

PREVIOUSLY UNREPORTED SUBSTANCE (P<0.05)

Figure 3

Anion
SUBSTANCES THAT ACCUMULATE
WITH REDUCTION IN eGFR

| Compound | Spearman correlation coefficients | p value |
|---|---|---|
| Isethionate | -0.929 | <0.001 |
| Gluconate | -0.929 | <0.001 |
| trans-Aconitate | -0.869 | <0.001 |
| Pimelate | -0.847 | <0.001 |
| 3-Indoxyl sulfate | -0.834 | <0.001 |
| Isocitrate | -0.825 | <0.001 |
| N-Acetyl-beta-alanine | -0.805 | <0.001 |
| N-Acetylglutamate | -0.782 | <0.001 |
| Sebacate | -0.751 | <0.001 |
| 2-Oxopentanoate | -0.725 | <0.001 |
| cis-Aconitate | -0.719 | <0.001 |
| Homovanillate | -0.711 | <0.001 |
| Adipate | -0.677 | <0.001 |
| Citramalate | -0.670 | <0.001 |
| 2-Isopropylmalate | -0.669 | <0.001 |
| Threonate | -0.631 | <0.001 |
| Hippurate | -0.608 | <0.001 |
| N-Acetylaspartate | -0.594 | <0.001 |
| 4-Hydroxy-3-methoxymandelate | -0.572 | <0.001 |
| Oxamate | -0.559 | <0.001 |
| Glutarate | -0.465 | 0.003 |
| Azelate | -0.463 | 0.003 |
| Phthalate | -0.456 | 0.003 |
| citrate | -0.454 | 0.004 |
| Malonate | -0.440 | 0.005 |
| Citraconate | 0.401 | 0.011 |
| Quinate | -0.392 | 0.013 |
| Succinate | -0.362 | 0.021 |
| Cysteine S-sulfate | -0.343 | 0.030 |
| 2-Hydroxy-3-methoxybenzoate | -0.322 | 0.041 |
| Glycerophosphate | -0.284 | 0.072 |
| 2-Hydroxyoctarate | -0.208 | 0.189 |
| Malate | -0.157 | 0.321 |
| 2-Hydroxypentanoate | -0.139 | 0.379 |
| Heptanoate | -0.128 | 0.416 |
| Laurate | -0.100 | 0.527 |
| 5-Oxoproline | -0.067 | 0.671 |
| Mucate | -0.064 | 0.686 |

SUBSTANCES THAT DECREASE WITH
REDUCTION IN eGFR

| Compound | Spearman correlation coefficients | p value |
|---|---|---|
| 4-Methyl-2-oxopentanoate | 0.673 | <0.001 |
| 2-Oxoisopentanoate | 0.645 | <0.001 |
| Lactate | 0.349 | 0.027 |
| Octanoate | 0.348 | 0.027 |
| 2-Oxoglutarate | 0.331 | 0.036 |
| Pyruvate | 0.305 | 0.053 |
| 2-Hydroxyisobutyrate,2-Hydroxybutyrate | 0.226 | 0.152 |
| Fumarate | 0.155 | 0.327 |
| 3-Hydroxybutyrate | 0.094 | 0.553 |
| Pelargonate | 0.063 | 0.689 |
| Pentanoate,3-Methylbutanoate | 0.021 | 0.892 |
| Decanoate | 0.015 | 0.923 |
| Hexanoate | 0.011 | 0.946 |

PREVIOUSLY UNREPORTED SUBSTANCE (P<0.05)

N-acetylglucosamine

HUMAN RENAL DISEASE MARKER SUBSTANCE

TECHNICAL FIELD

The present invention relates to a method for determining a renal disease using a novel renal disease marker substance in human and a method for screening for a prophylactic/therapeutic agent for a renal disease using the renal disease marker substance.

BACKGROUND ART

The number of patients with a renal disease such as patients with renal failure, particularly the number of patients undergoing renal dialysis is constantly on the rise every year. At present, two hundred thousand patients receive maintenance dialysis therapy, and an additional thirty thousand or more people start dialysis every year. The annual cost of dialysis therapy is approximately five million yen per individual, meaning that medical care cost of approximately a trillion yen is constantly required for two hundred thousand people. Also, recently, a disease concept of Chronic Kidney Disease (CKD) has been proposed, raising awareness of the importance of prevention and treatment of CKD. In light of the fact that CKD is a common disease with the population of people having a glomerular filtration rate (GFR) of less than 60 reaching as high as 19.26 million, countermeasures against CKD are urgently needed. Under the foregoing circumstances, if a preventive method for symptoms of a renal disease such as renal failure and CKD and a therapeutic method capable of alleviating such symptoms and delaying introduction of dialysis can be developed, then not only a contribution is made to Quality Of Life (QOL) of the patients but also medical care cost can be reduced considerably, making a great contribution to the society.

When an individual suffers from renal failure, various substances that would be excreted from the kidney in a healthy state accumulate in the body. These substances are occasionally utilized as marker substances in the diagnosis of renal failure. For example, a method of detecting/diagnosing a renal disease by using an increase in a marker protein for a renal disease such as albumin excreted in urine as an index is commonly employed. As other methods, for example, a method for detecting a renal disease utilizing an elevated blood concentration of human lipocalin-type prostaglandin D synthase in patients with a renal disease (see patent document 1) and a method for diagnosing nephropathy utilizing elevated blood and urinary concentrations of ENDO180 receptor polypeptide in patients with renal failure and the like (see patent document 2) are known.

Also, among the aforementioned substances that accumulate in the body of an individual suffering from renal failure, a substance that is toxic to the living body is referred to as a so-called renal failure substance, which has been reported as a substance that aggravates the pathological condition of renal failure per se. However, most of the presently used renal failure marker substances such as creatinine reflect glomerular filtration rate (GFR), where glomerular filtration is a part of renal function, and few of them reflect other renal functions such as tubular function. Also, because creatinine has a creatinine blind GFR area, which does not reflect renal function (i.e., a period in which an increase in creatinine remains unrecognizable despite aggravation of renal function), it has been unsatisfactory as a renal failure marker substance. Further, it is difficult to evaluate various symptoms of renal failure in an integrated fashion with the existing marker substances. Also, substances involved in aggravation of renal failure and the mechanism of aggravation of renal failure have remained largely unknown.

Meanwhile, capillary electrophoresis mass spectrometry (CE-MS) is a recently developed new system, which enables simultaneous measurement of 500 or more kinds of substances from a small amount of sample.

PRIOR ART DOCUMENTS

Patent Document

[Patent document 1] Japanese unexamined Patent Application Publication No. 2000-146980
[Patent document 2] Japanese unexamined Patent Application Publication (Translation of PCT Application) No. 2007-519394

SUMMARY OF THE INVENTION

Object to be Solved by the Invention

An object of the present invention is to provide a method capable of accurately determining even a renal disease that could not have been detected by various conventional renal disease test methods with a reduced burden on a subject (a donor of a test sample). Another object of the present invention is to provide a method capable of determining an early stage renal disease, focusing on a renal disease marker substance with a small blind GFR area. Further, another object of the present invention is to provide a novel method for screening for a prophylactic/therapeutic agent for a renal disease capable of efficiently screening for a novel prophylactic/therapeutic agent for a renal disease that focused on a new, previously unnoticed renal disease marker substance.

Means to Solve the Object

The present inventors have comprehensively analyzed the substances in the plasma of patients with a renal disease (cationic and anionic substances) by CE-MS, and identified substances that are found to be significantly correlated with estimated glomerular filtration rate (eGFR) either positively or negatively. The present inventors have found that, among these substances, there are substances whose association with a renal disease has been hitherto unknown and substances whose correlation equation with respect to eGFR approximates to a linear equation, thereby completing the present invention.

That is, the present invention relates to (1) a method for determining a renal disease, comprising the step of detecting or quantifying cis-aconitate present in a test blood sample, (2) the method for determining a renal disease according to the aforementioned (1), further comprising the step of comparing the result of detection or quantification of cis-aconitate present in the test blood sample with that of a control to determine whether a donor of the test blood sample has a renal disease, or to evaluate a degree of symptoms of a renal disease of the donor, (3) the method for determining a renal disease according to the aforementioned (2), wherein the donor of the test blood sample is identified as having a renal disease when a concentration of cis-aconitate present in the test blood sample is higher than that of a control, or the degree of severity of symptoms of a renal disease of the donor is evaluated to be equivalent to a degree by which a concentration of cis-aconitate present in the test blood sample exceeds a control, (4) the method for determining a renal disease according to any one of the aforementioned (1) to (3), wherein the the renal disease is renal failure, (5) a method for determining an early stage renal disease, comprising the step of detecting or quantifying cis-aconitate present in a test blood sample, and (6) the method for determining an early stage renal disease according to the aforementioned (5), wherein the renal disease is renal failure.

The present invention also relates to (7) a method for screening for a prophylactic/therapeutic agent for a renal disease, comprising the following steps A) to D): A) administering a test substance to a non-human animal with reduced renal function; B) collecting a blood sample from the non-human animal; C) detecting or quantifying cis-aconitate present in the blood sample; and D) comparing the result of detection or quantification of cis-aconitate present in the blood sample with that of a control to evaluate renal function of the non-human animal.

As used herein, for the sake of convenience, the terms "a subject", "a donor of a test sample", "a patient without a renal disease", and "a healthy individual" include humans as well as other non-human animals, and humans and non-human mammals are preferred, and humans are more preferred.

Effect of the Invention

The method for determining a renal disease of the present invention enables accurate determination of even a renal disease that could not have been detected by various conventional renal disease test methods with a reduced burden on a subject (a donor of a test sample). Also, it is considered that when progress is made in the research of the renal disease marker substance that was discovered for the first time by the present invention, it may be able to serve as a renal disease marker substance corresponding to various pathological conditions and symptoms of a renal disease. Also, the method for determining an early stage renal disease of the present invention enables determination of an early stage renal disease, which could not have been fully achieved by conventional renal disease marker substances. Also, the method for screening for a prophylactic/therapeutic agent for a renal disease of the present invention can efficiently screen for a novel prophylactic/therapeutic agent for a renal disease that focused on a new, previously unnoticed renal disease marker substance.

BRIEF DESCRIPTION OF DRAWINGS

FIG. 1 is a diagram showing the background of 41 patients with a renal disease (patients with chronic kidney).

FIG. 2 is a diagram showing cations found to be positively or negatively correlated with eGFR in plasma. The table on the left shows cations found to be significantly negatively correlated with eGFR by the Spearman's correlation coefficient, and the table on the right shows cations found to be significantly positively correlated with eGFR. It is to be noted that the names of the substances having newly discovered, significant correlation with eGFR are shown with a gray background.

FIG. 3 is a diagram showing anions found to be positively or negatively correlated with eGFR in plasma. The table on the left shows anions found to be significantly negatively correlated with eGFR and the table on the right shows anions found to be significantly positively correlated with eGFR. It is to be noted that the names of the substances whose correlation with eGFR was newly discovered are shown with a gray background. Here, the substance negatively correlated with eGFR is a substance whose concentration decreases with an improvement in renal function, i.e., a substance whose concentration increases with a deterioration in renal function. Also, the substance positively correlated with eGFR is a substance whose concentration increases with an improvement in renal function, i.e., a substance whose concentration decreases with a deterioration in renal function.

MODE OF CARRYING OUT THE INVENTION

The method for determining a renal disease of the present invention (first embodiment of the present invention)

The method for determining a renal disease of the present invention is not particularly limited as long as it includes the step of detecting or quantifying one or two or more renal disease marker substances present in a test blood sample, selected from the following renal disease marker substances (hereinbelow, may also be expressed as "the present renal disease marker substance"). (Cationic renal disease marker substances negatively correlated with eGFR): N-acetylglucosamine, γ-butyrobetaine, ophthalmate, N-ε-acetyllysine, cytosine, hypotaurine, 7-methylguanine, methionine sulfoxide, and asparagine (Asn);

(Cationic renal disease marker substances positively correlated with eGFR): 2-aminobutyrate and glutamic acid (Glu);

(Anionic renal disease marker substances negatively correlated with eGFR): isethionate, gluconate, trans-aconitate, pimelate, isocitrate, N-acetyl-β-alanine, N-acetylglutamate, sebacate, 4-oxopentanoate, cis-aconitate, homovanillate, adipate, citramalate, 2-isopropylmalate, threonate, N-acetylaspartate, 4-hydroxy-3-methoxymandelate, oxamate, glutarate, azetate, phthalate, malonate, citraconate, quinate, succinate, cysteine S-sulfate, and 4-hydroxy-3-methoxybenzoate;

(Anionic renal disease marker substances positively correlated with eGFR): 4-methyl-2-oxopentanoate, 2-oxoisopentanoate, lactate, octanoate, and 2-oxoglutarate. It should be noted that, from the viewpoint of further increasing the accuracy of the method for determining a renal disease of the present invention, a method of concomitantly using two or more kinds of the present renal disease marker substances is also possible.

The method for determining a renal disease of the present invention can determine whether a donor of a test blood sample has a renal disease, or evaluate a degree of symptoms of a renal disease of the donor.

Among the present renal disease marker substances described above, preferred examples of the marker substances having higher correlation coefficients for estimated glomerular filtration rate (eGFR) include N-acetylglucosamine, γ-butyrobetaine, N-ε-acetyllysine, cytosine, and oxamate; 2-aminobutyrate and glutamic acid; isethionate, gluconate, trans-aconitate, pimelate, isocitrate, N-acetyl-β-alanine, N-acetylglutamate, sebacate, 4-oxopentanoate, cis-aconitate, homovanillate, adipate, citramalate, 2-isopropylmalate, threonate, N-acetylaspartate, and 4-hydroxy-3-methoxymandelate; and 4-methyl-2-oxopentanoate and 2-oxoisopentanoate.

Figure 5:
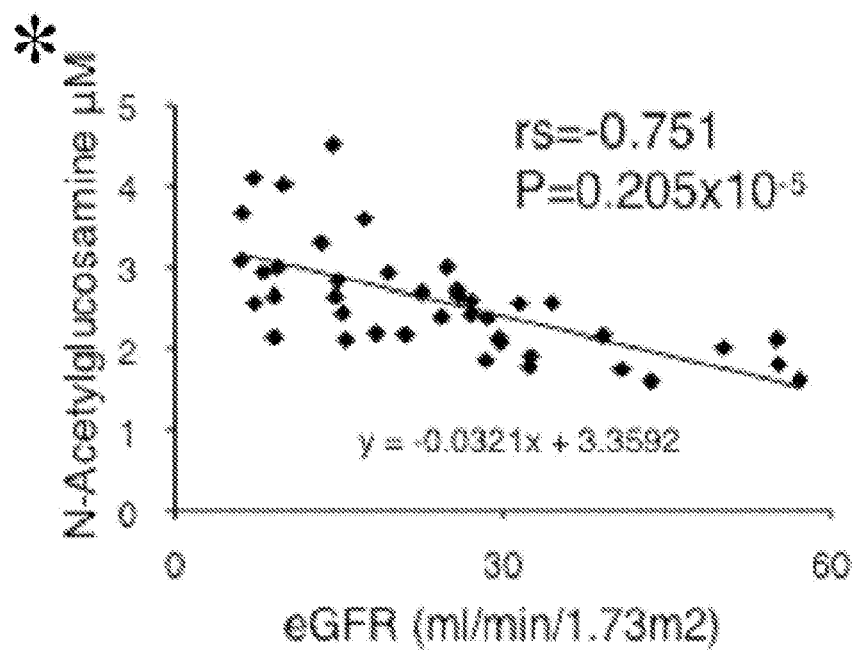
FIG. 5 is a graph showing the correlation between the concentration of a cation found to be negatively correlated with eGFR and eGFR. The correlation was approximated to a linear equation. Also, the asterisk "*" indicates a substance whose negative correlation with eGFR was discovered for the first time.
Figure 6:
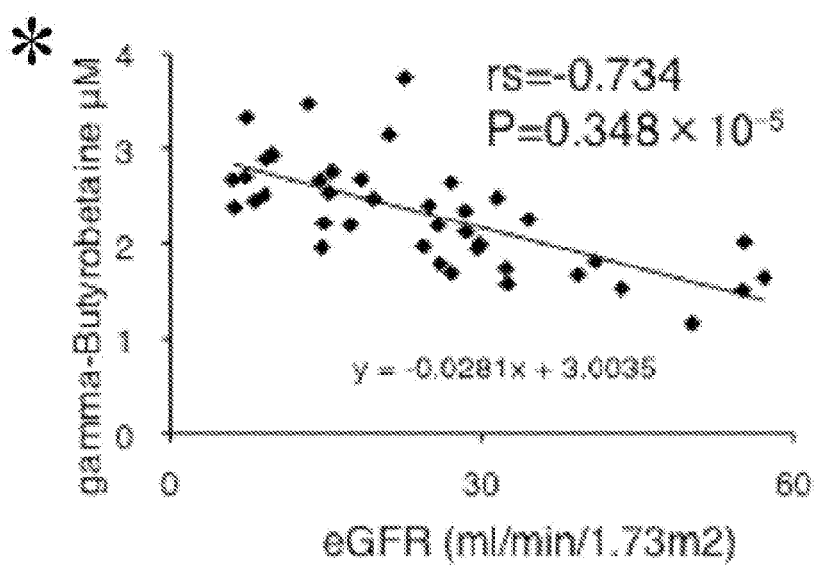
FIG. 6 is a graph showing the correlation between the concentration of a cation found to be negatively correlated with eGFR and eGFR. The correlation was approximated to a linear equation. Also, the asterisk "*" indicates a substance whose negative correlation with eGFR was discovered for the first time.
Figure 7:
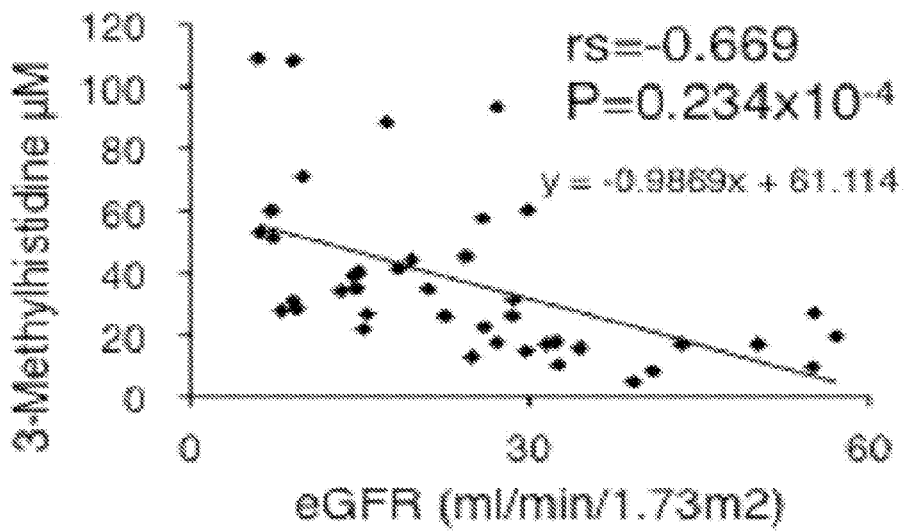
FIG. 7 is a graph showing the correlation between the concentration of a cation found to be negatively correlated with eGFR and eGFR. The correlation was approximated to a linear equation.
Figure 8:
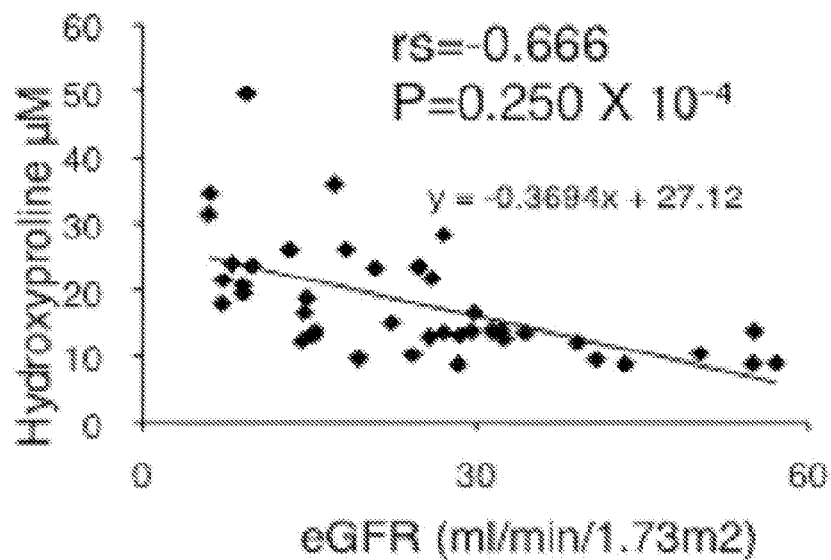
FIG. 8 is a graph showing the correlation between the concentration of a cation found to be negatively correlated with eGFR and eGFR. The correlation was approximated to a linear equation.
Figure 9:
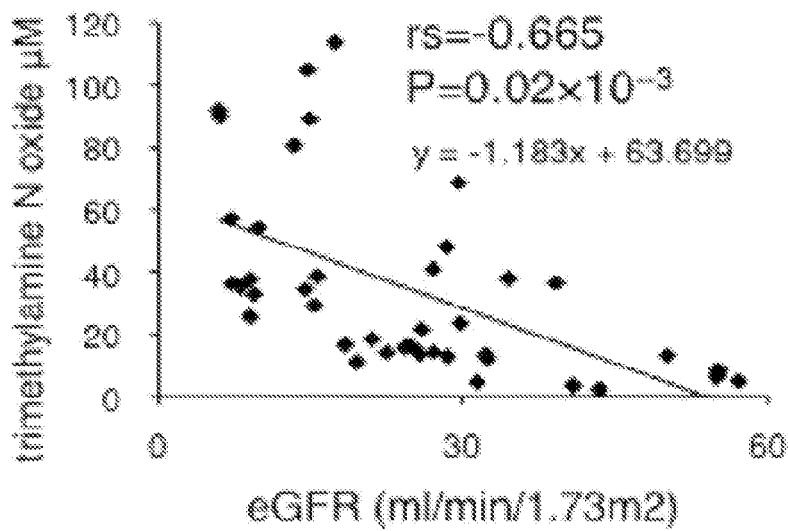
FIG. 9 is a graph showing the correlation between the concentration of a cation found to be negatively correlated with eGFR and eGFR. The correlation was approximated to a linear equation.
Figure 10:
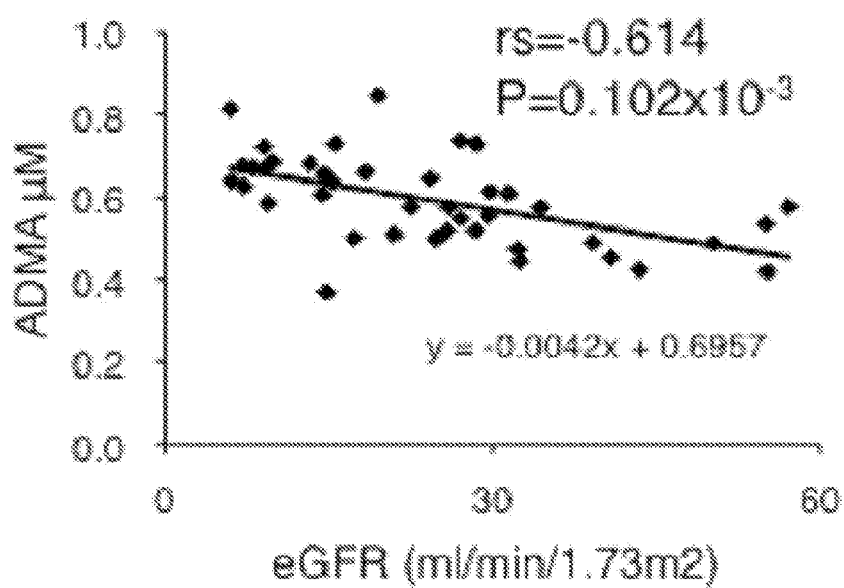
FIG. 10 is a graph showing the correlation between the concentration of a cation found to be negatively correlated with eGFR and eGFR. The correlation was approximated to a linear equation.
Figure 11:
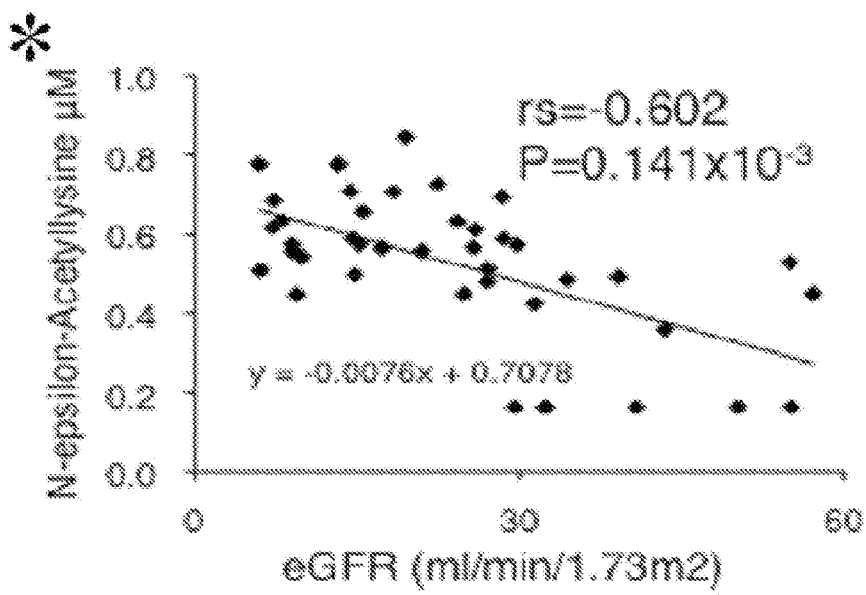
FIG. 11 is a graph showing the correlation between the concentration of a cation found to be negatively correlated with eGFR and eGFR. The correlation was approximated to a linear equation. Also, the asterisk "*" indicates a substance whose negative correlation with eGFR was discovered for the first time.
Figure 12:
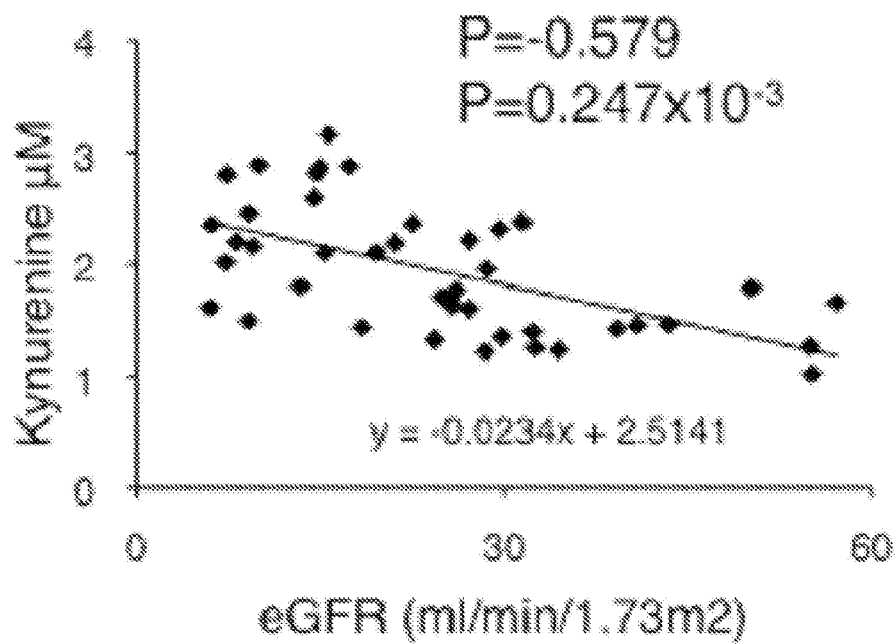
FIG. 12 is a graph showing the correlation between the concentration of a cation found to be negatively correlated with eGFR and eGFR. The correlation was approximated to a linear equation.
Figure 13:
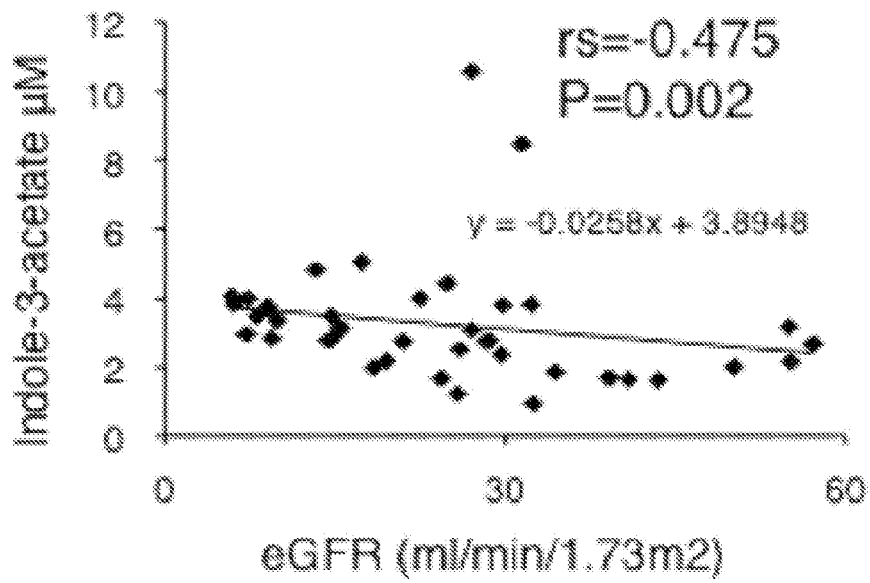
FIG. 13 is a graph showing the correlation between the concentration of a cation found to be negatively correlated with eGFR and eGFR. The correlation was approximated to a linear equation.
Figure 14:
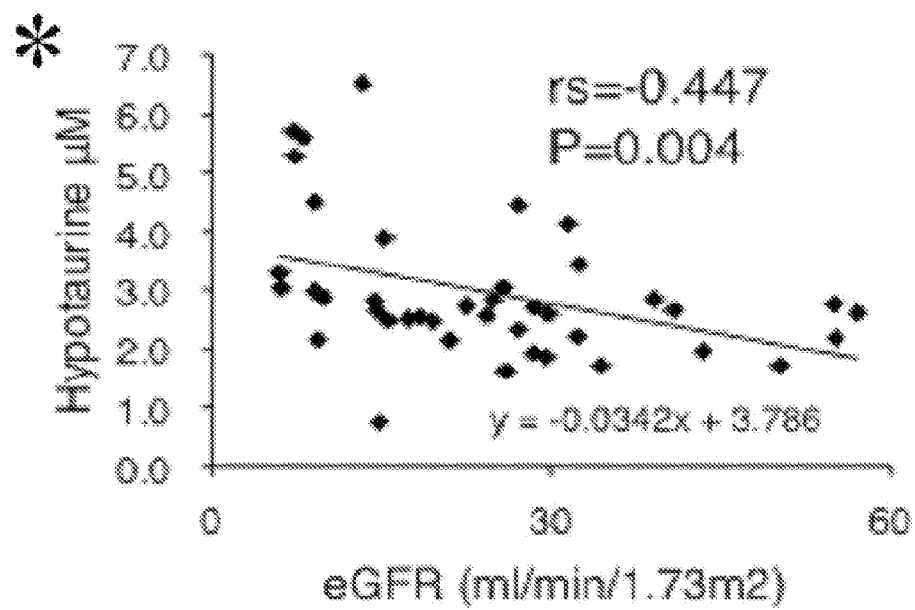
FIG. 14 is a graph showing the correlation between the concentration of a cation found to be negatively correlated with eGFR and eGFR. The correlation was approximated to a linear equation. Also, the asterisk "*" indicates a substance whose negative correlation with eGFR was discovered for the first time.
Figure 15:
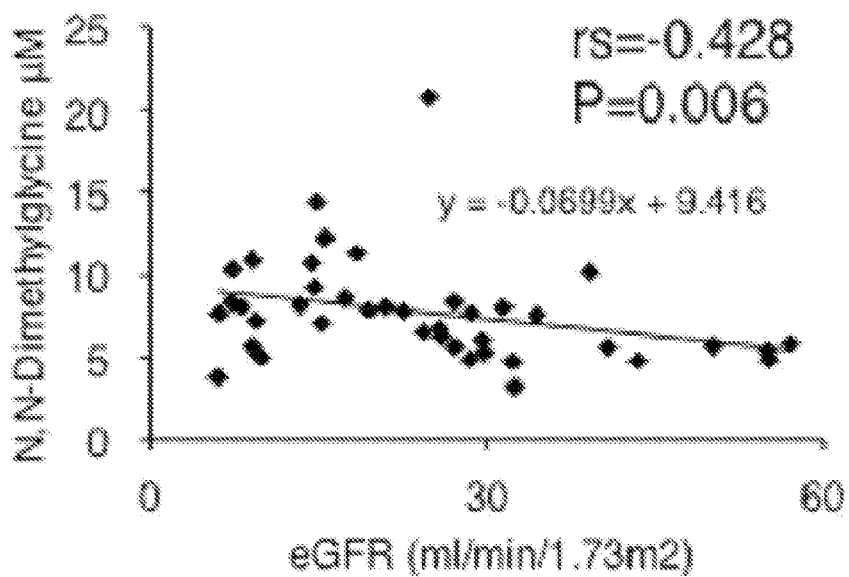
FIG. 15 is a graph showing the correlation between the concentration of a cation found to be negatively correlated with eGFR and eGFR. The correlation was approximated to a linear equation.
Figure 16:
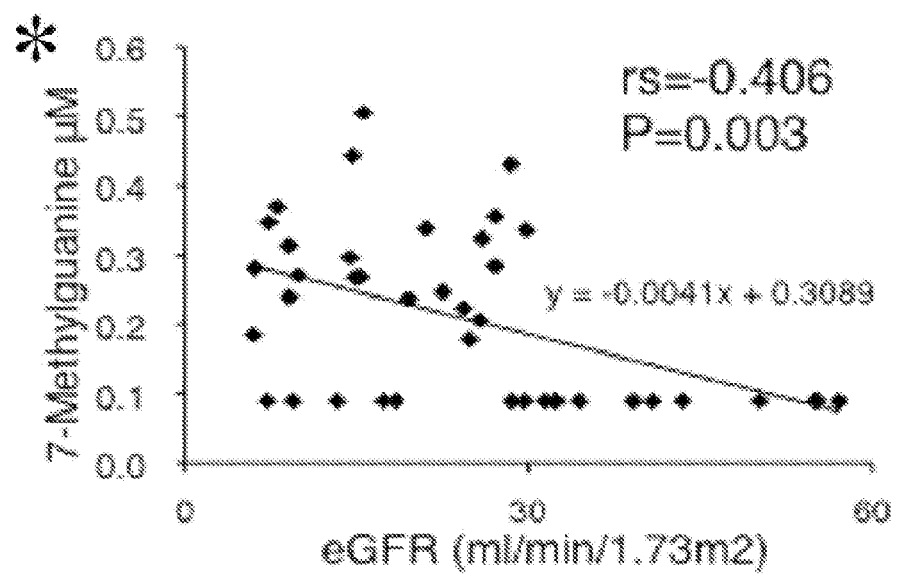
FIG. 16 is a graph showing the correlation between the concentration of a cation found to be negatively correlated with eGFR and eGFR. The correlation was approximated to a linear equation. Also, the asterisk "*" indicates a substance whose negative correlation with eGFR was discovered for the first time.
Figure 17:
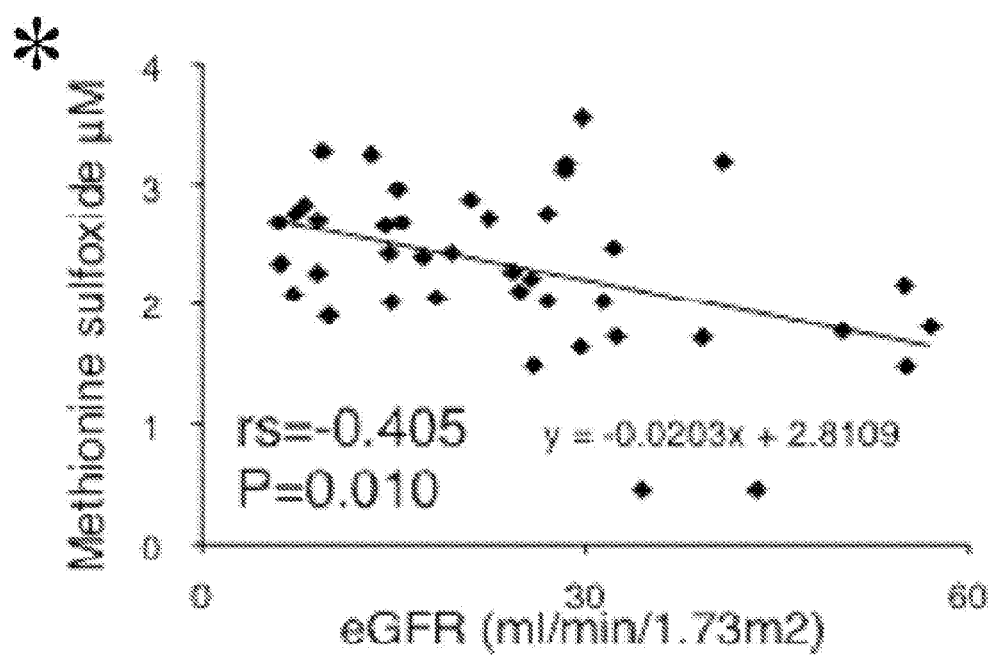
FIG. 17 is a graph showing the correlation between the concentration of a cation found to be negatively correlated with eGFR and eGFR. The correlation was approximated to a linear equation. Also, the asterisk "*" indicates a substance whose negative correlation with eGFR was discovered for the first time.
Figure 18:
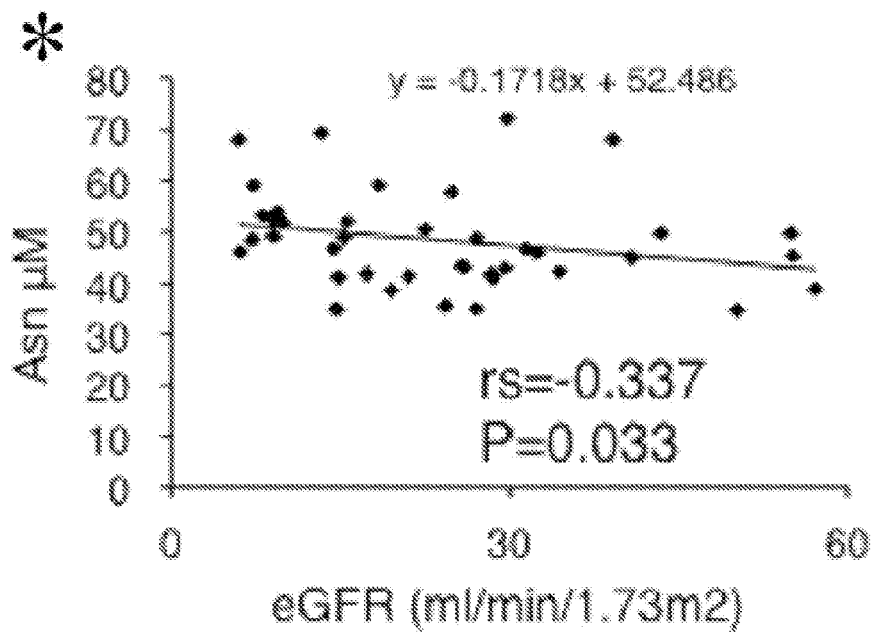
FIG. 18 is a graph showing the correlation between the concentration of a cation found to be negatively correlated with eGFR and eGFR. The correlation was approximated to a linear equation. Also, the asterisk "*" indicates a substance whose negative correlation with eGFR was discovered for the first time.
Figure 27:
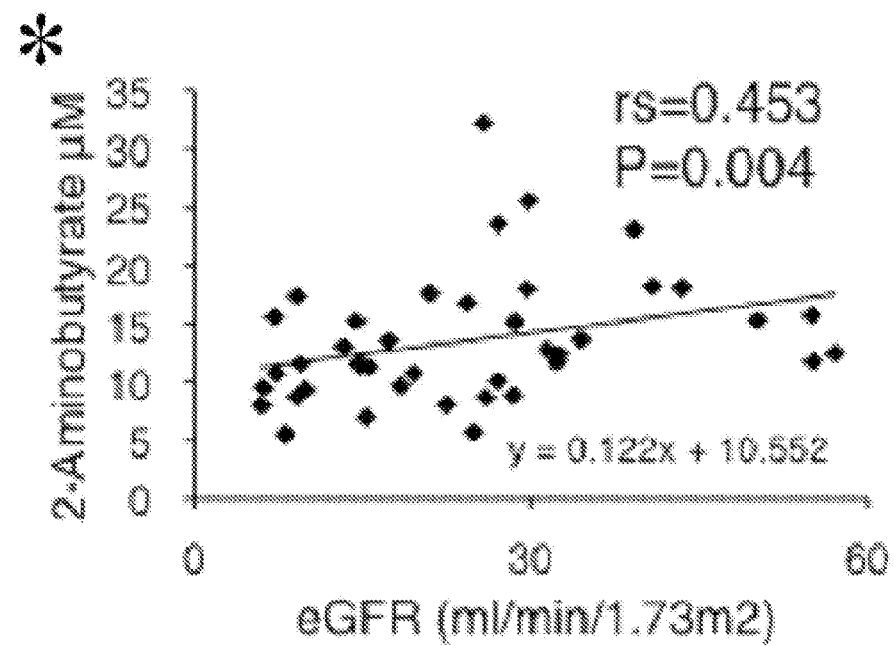
FIG. 27 is a graph showing the correlation between the concentration of a cation found to be positively correlated with eGFR and eGFR. The correlation was approximated to a linear expression. Also, the asterisk "*" indicates a substance whose negative correlation with eGFR was discovered for the first time.
Figure 28:
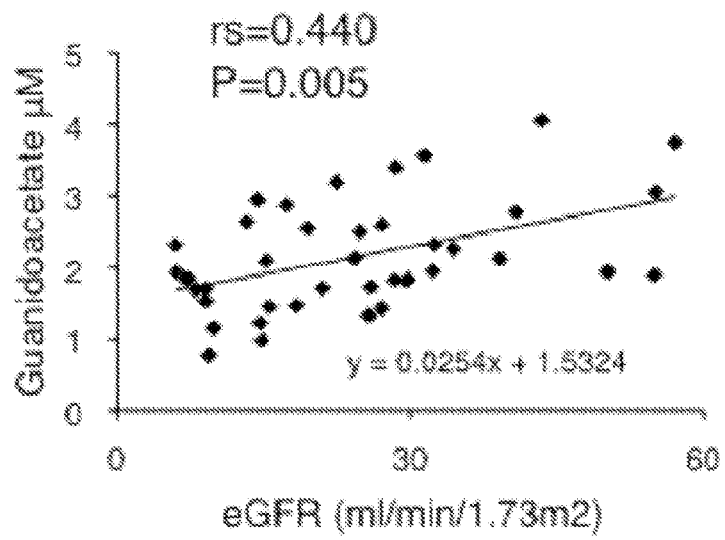
FIG. 28 is a graph showing the correlation between the concentration of a cation found to be positively correlated with eGFR and eGFR. The correlation was approximated to a linear expression.
Figure 29:
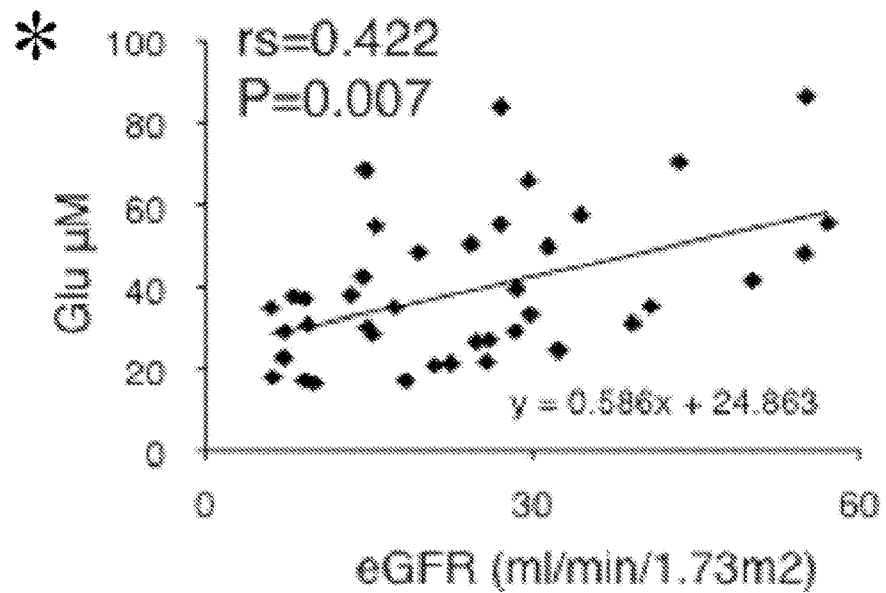
FIG. 29 is a graph showing the correlation between the concentration of a cation found to be positively correlated with eGFR and eGFR. The correlation was approximated to a linear expression. Also, the asterisk "*" indicates a substance whose negative correlation with eGFR was discovered for the first time.
Figure 30:
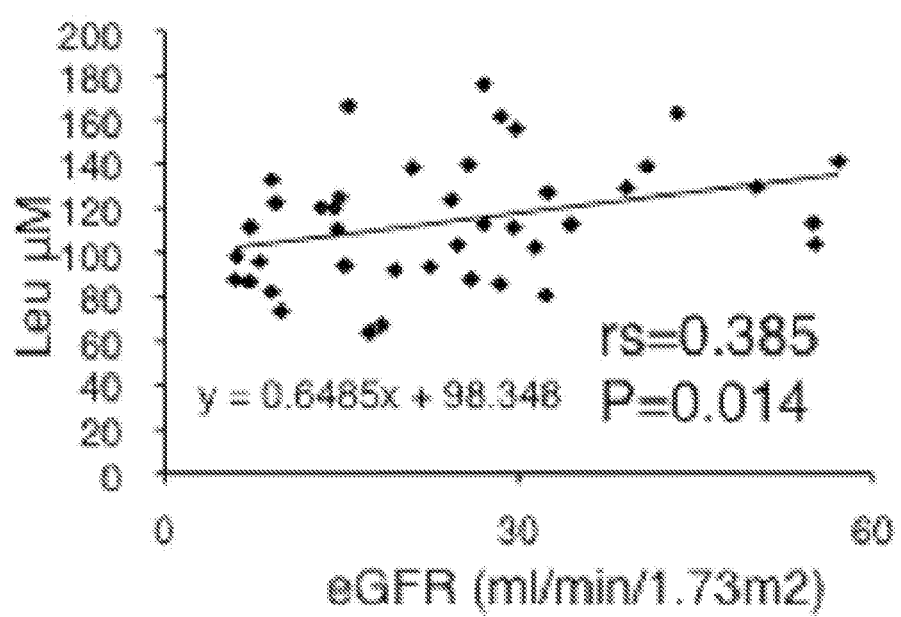
FIG. 30 is a graph showing the correlation between the concentration of a cation found to be positively correlated with eGFR and eGFR. The correlation was approximated to a linear expression.
Figure 31:
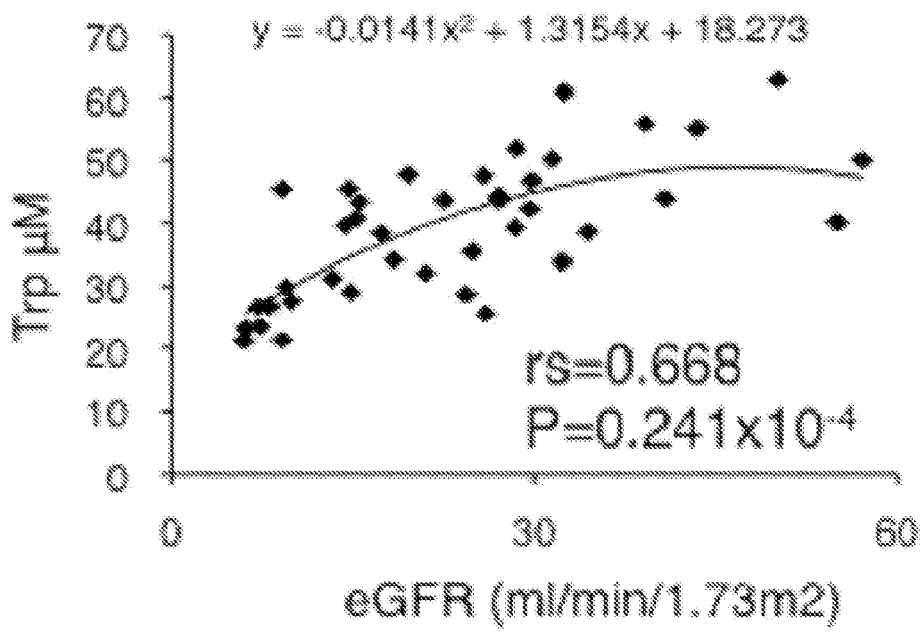
FIG. 31 is a graph showing the correlation between the concentration of a cation found to be positively correlated with eGFR and eGFR. The correlation was approximated to a quadratic equation.
Figure 32:
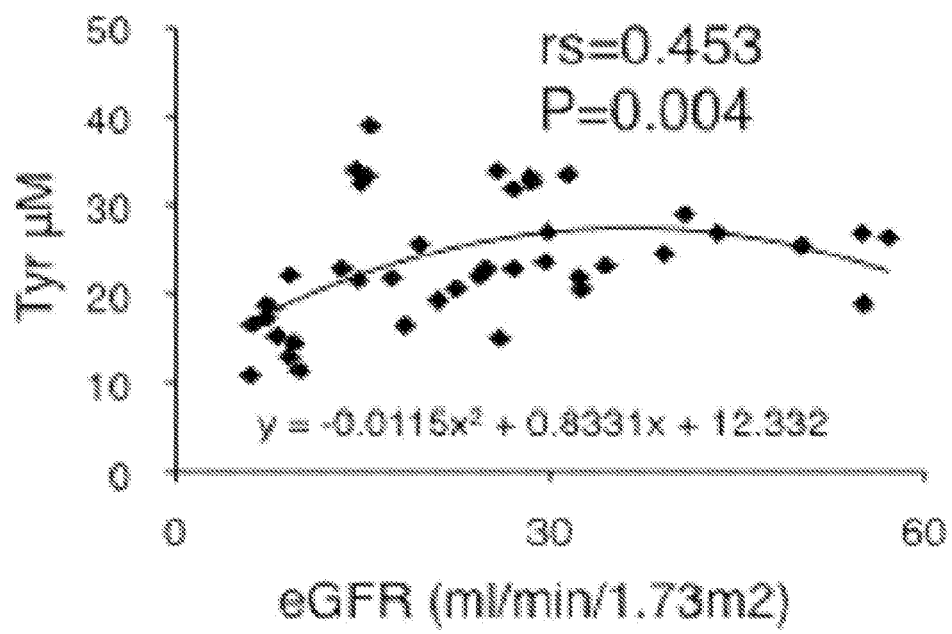
FIG. 32 is a graph showing the correlation between the concentration of a cation found to be positively correlated with eGFR and eGFR. The correlation was approximated to a quadratic equation.
Figure 33:
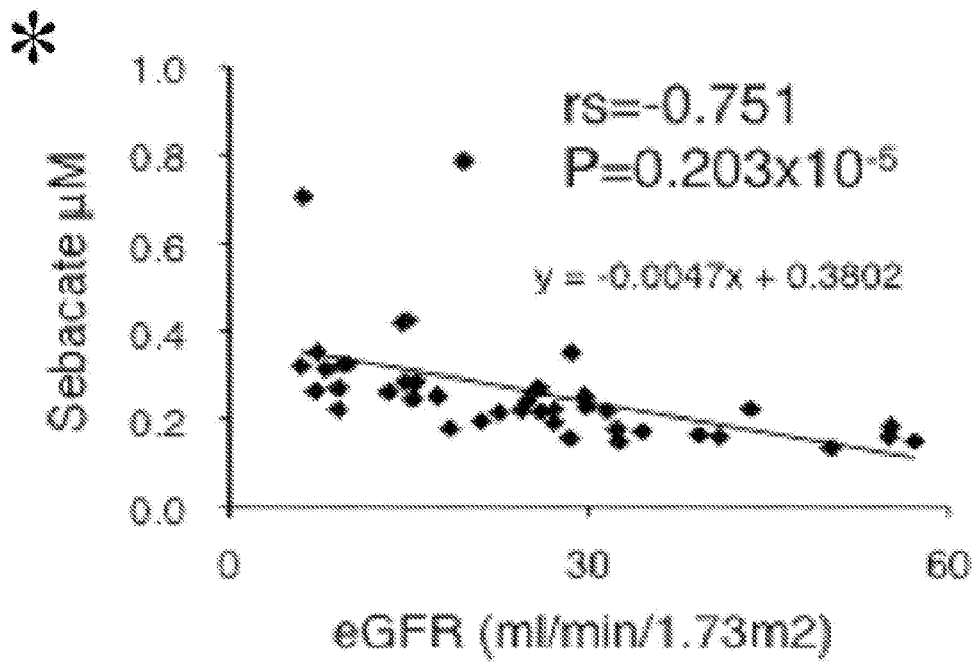
FIG. 33 is a graph showing the correlation between the concentration of an anion found to be negatively correlated with eGFR and eGFR. The correlation was approximated to a linear expression. Also, the asterisk "*" indicates a substance whose negative correlation with eGFR was discovered for the first time.
Figure 34:
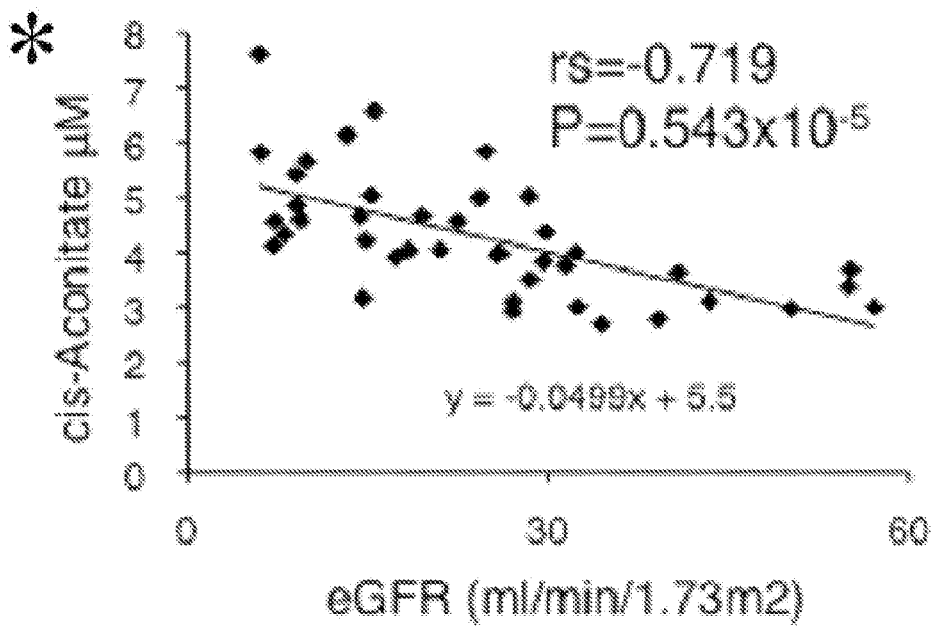
FIG. 34 is a graph showing the correlation between the concentration of an anion found to be negatively correlated with eGFR and eGFR. The correlation was approximated to a linear expression. Also, the asterisk "*" indicates a substance whose negative correlation with eGFR was discovered for the first time.
Figure 35:
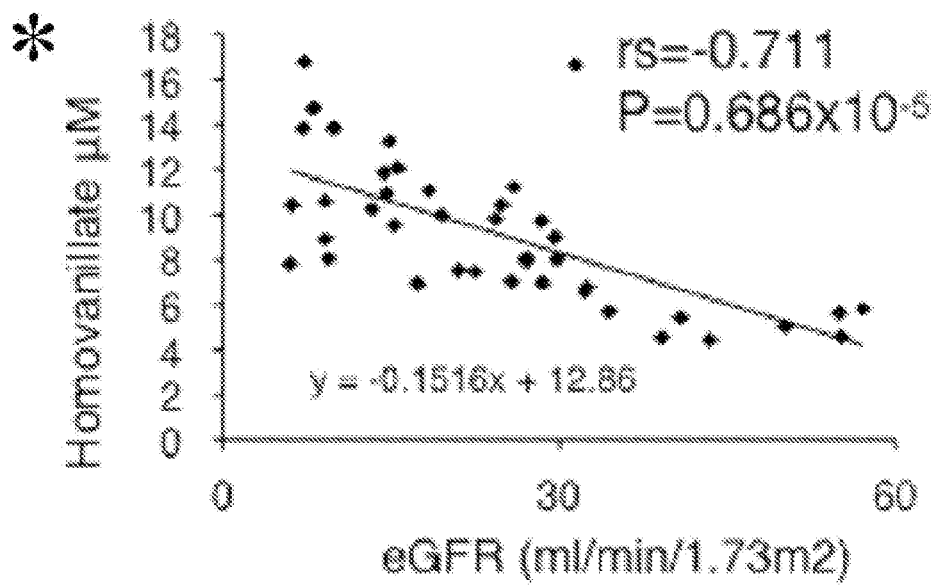
FIG. 35 is a graph showing the correlation between the concentration of an anion found to be negatively correlated with eGFR and eGFR. The correlation was approximated to a linear expression. Also, the asterisk "*" indicates a substance whose negative correlation with eGFR was discovered for the first time.
Figure 36:
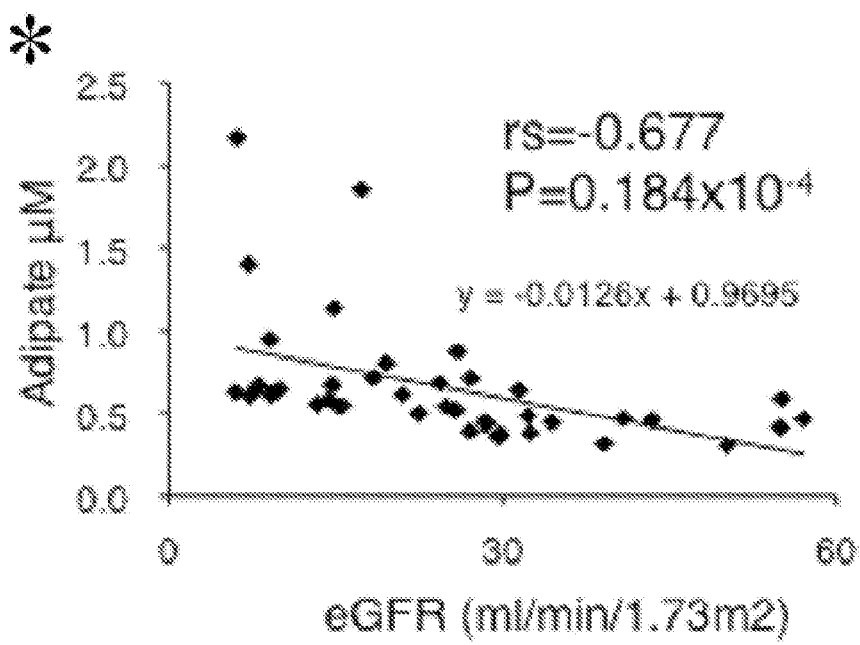
FIG. 36 is a graph showing the correlation between the concentration of an anion found to be negatively correlated with eGFR and eGFR. The correlation was approximated to a linear expression. Also, the asterisk "*" indicates a substance whose negative correlation with eGFR was discovered for the first time.
Figure 37:
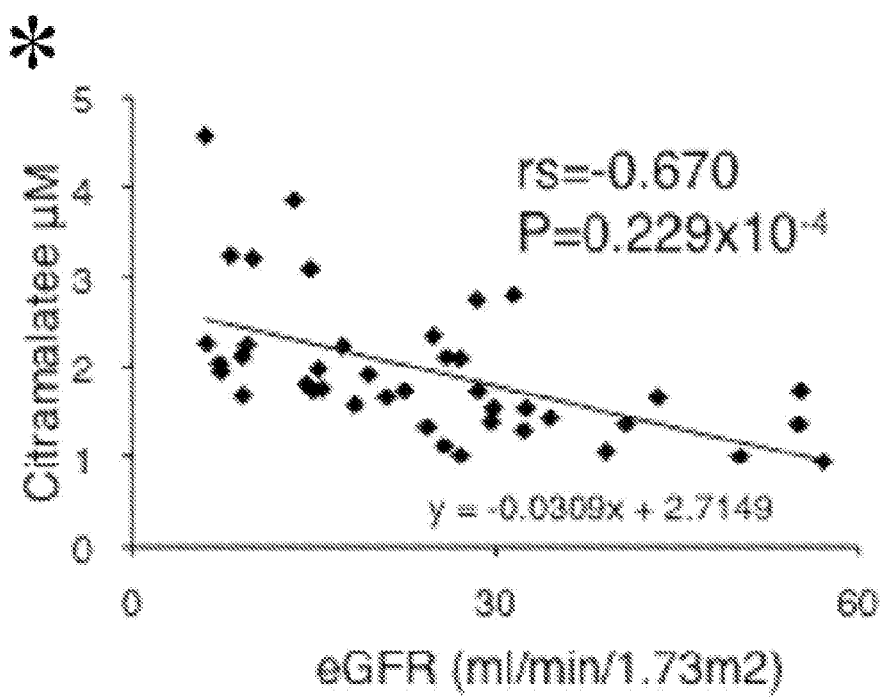
FIG. 37 is a graph showing the correlation between the concentration of an anion found to be negatively correlated with eGFR and eGFR. The correlation was approximated to a linear expression. Also, the asterisk "*" indicates a substance whose negative correlation with eGFR was discovered for the first time.
Figure 38:
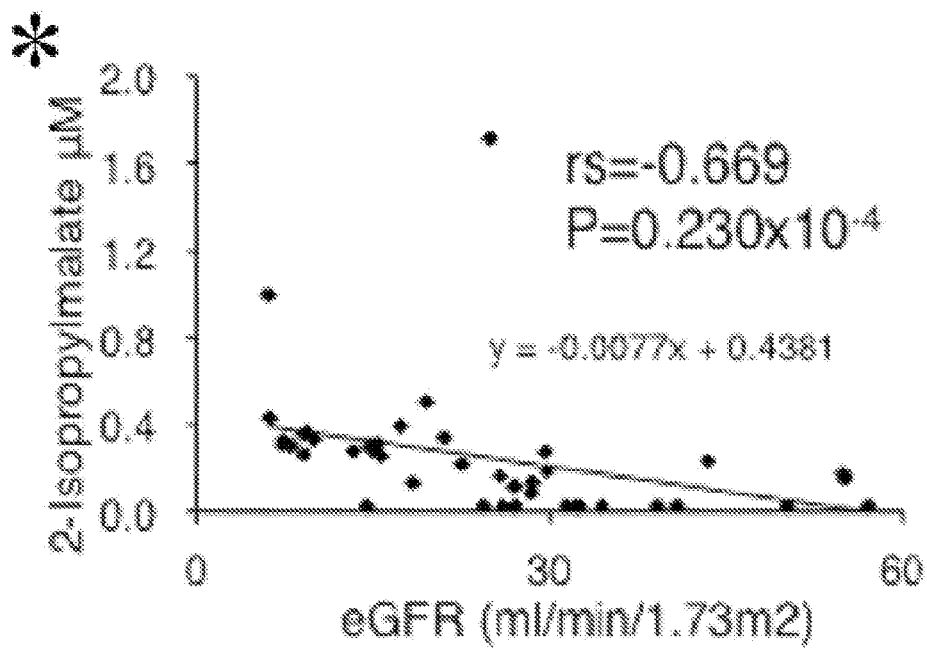
FIG. 38 is a graph showing the correlation between the concentration of an anion found to be negatively correlated with eGFR and eGFR. The correlation was approximated to a linear expression. Also, the asterisk "*" indicates a substance whose negative correlation with eGFR was discovered for the first time.
Figure 39:
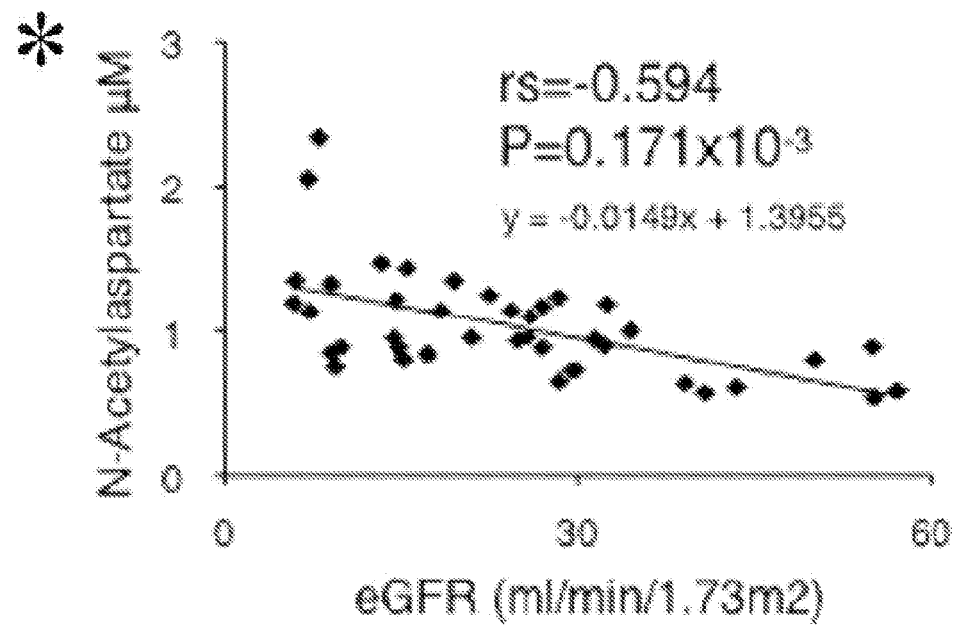
FIG. 39 is a graph showing the correlation between the concentration of an anion found to be negatively correlated with eGFR and eGFR. The correlation was approximated to a linear expression. Also, the asterisk "*" indicates a substance whose negative correlation with eGFR was discovered for the first time.
Figure 40:
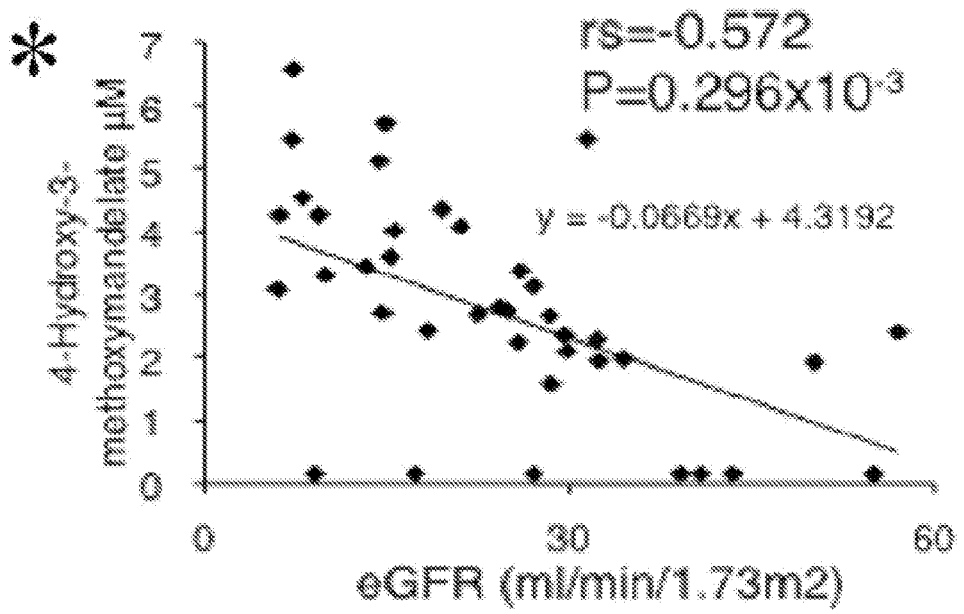
FIG. 40 is a graph showing the correlation between the concentration of an anion found to be negatively correlated with eGFR and eGFR. The correlation was approximated to a linear expression. Also, the asterisk "*" indicates a substance whose negative correlation with eGFR was discovered for the first time.
Figure 41:
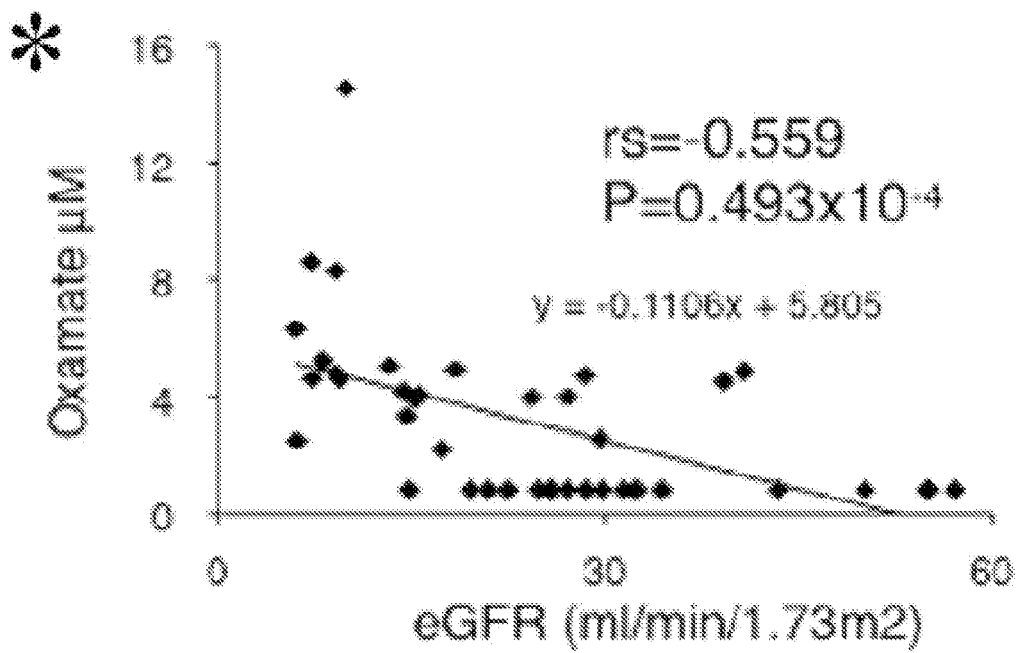
FIG. 41 is a graph showing the correlation between the concentration of an anion found to be negatively correlated with eGFR and eGFR. The correlation was approximated to a linear expression. Also, the asterisk "*" indicates a substance whose negative correlation with eGFR was discovered for the first time.
Figure 42:
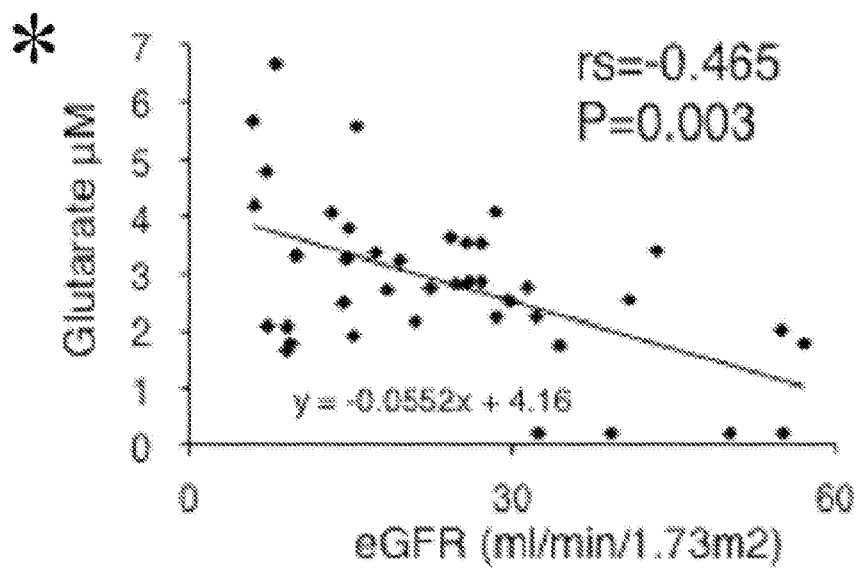
FIG. 42 is a graph showing the correlation between the concentration of an anion found to be negatively correlated with eGFR and eGFR. The correlation was approximated to a linear expression. Also, the asterisk "*" indicates a substance whose negative correlation with eGFR was discovered for the first time.
Figure 43:
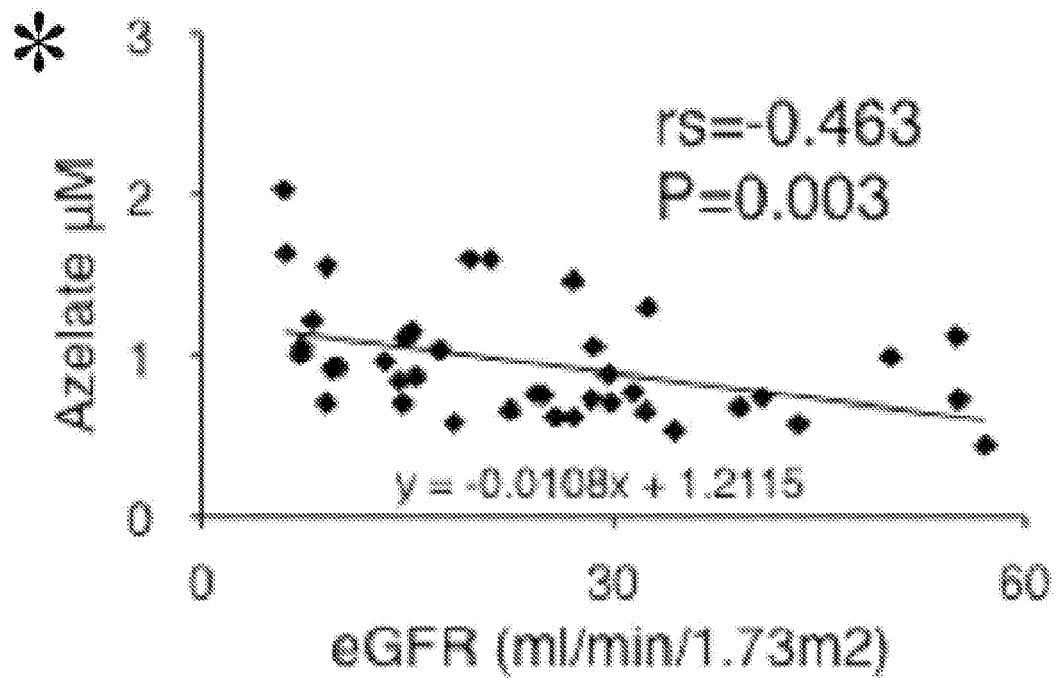
FIG. 43 is a graph showing the correlation between the concentration of an anion found to be negatively correlated with eGFR and eGFR. The correlation was approximated to a linear expression. Also, the asterisk "*" indicates a substance whose negative correlation with eGFR was discovered for the first time.
Figure 44:
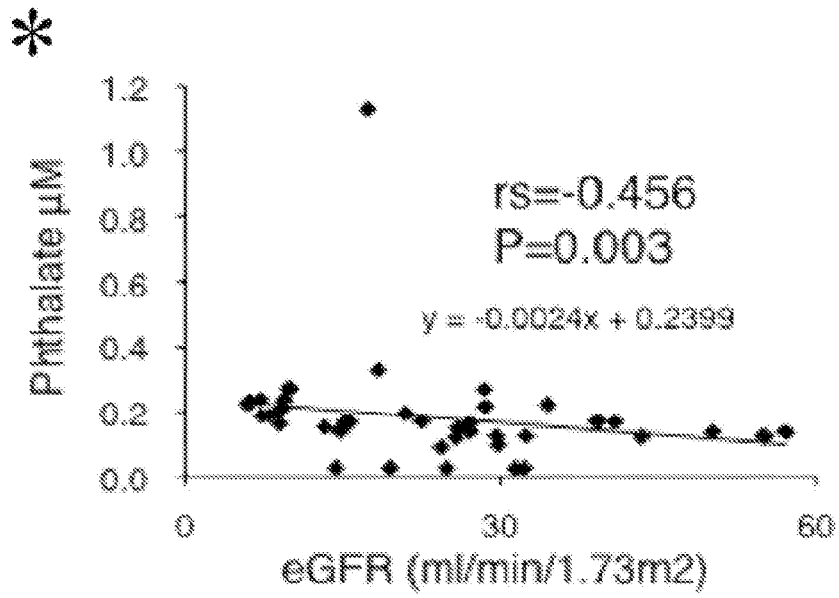
FIG. 44 is a graph showing the correlation between the concentration of an anion found to be negatively correlated with eGFR and eGFR. The correlation was approximated to a linear expression. Also, the asterisk "*" indicates a substance whose negative correlation with eGFR was discovered for the first time.
Figure 45:
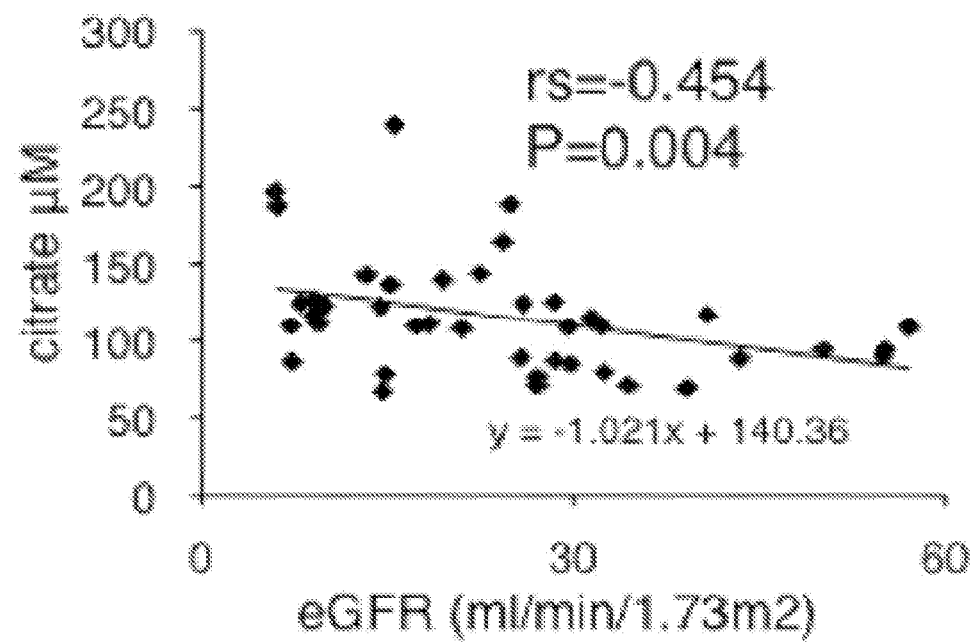
FIG. 45 is a graph showing the correlation between the concentration of an anion found to be negatively correlated with eGFR and eGFR. The correlation was approximated to a linear expression.
Figure 46:
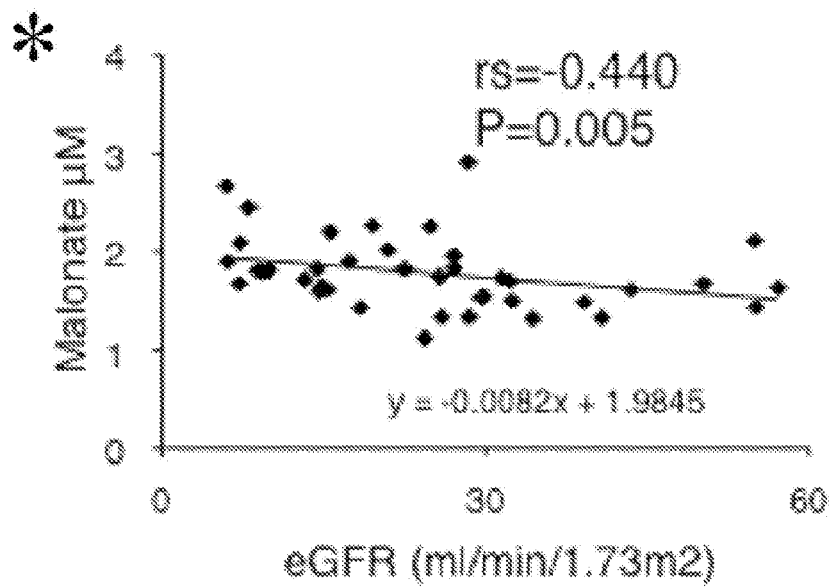
FIG. 46 is a graph showing the correlation between the concentration of an anion found to be negatively correlated with eGFR and eGFR. The correlation was approximated to a linear expression. Also, the asterisk "*" indicates a substance whose negative correlation with eGFR was discovered for the first time.
Figure 47:
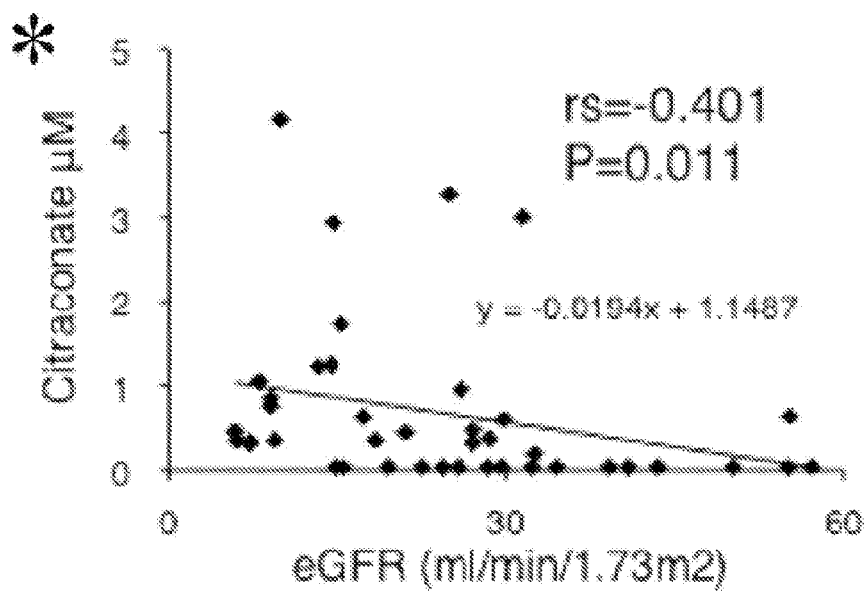
FIG. 47 is a graph showing the correlation between the concentration of an anion found to be negatively correlated with eGFR and eGFR. The correlation was approximated to a linear expression. Also, the asterisk "*" indicates a substance whose negative correlation with eGFR was discovered for the first time.
Figure 48:
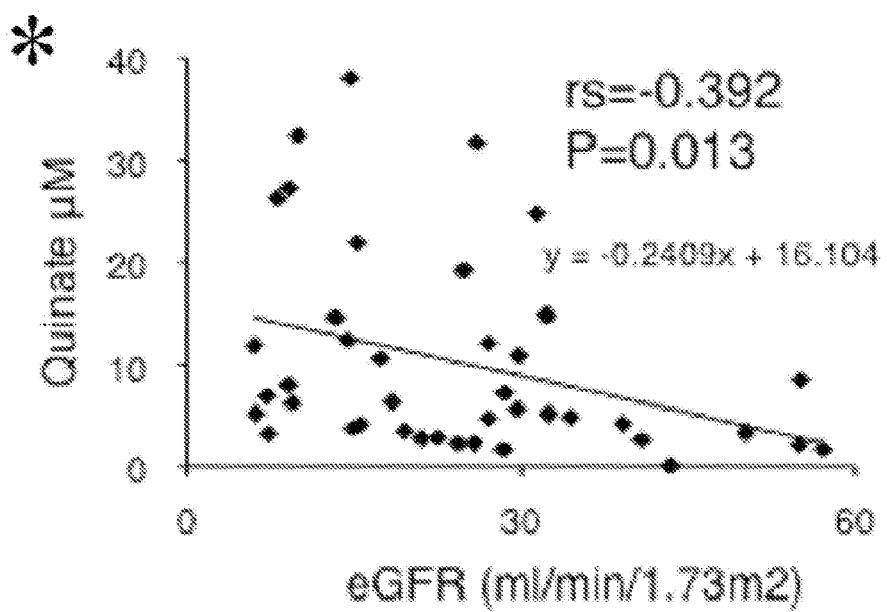
FIG. 48 is a graph showing the correlation between the concentration of an anion found to be negatively correlated with eGFR and eGFR. The correlation was approximated to a linear expression. Also, the asterisk "*" indicates a substance whose negative correlation with eGFR was discovered for the first time.
Figure 49:
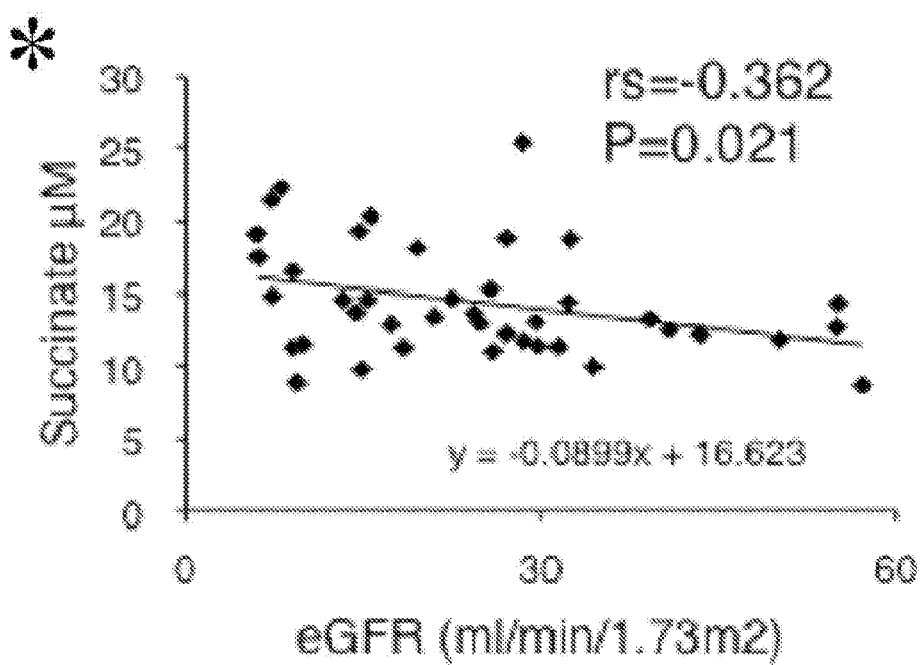
FIG. 49 is a graph showing the correlation between the concentration of an anion found to be negatively correlated with eGFR and eGFR. The correlation was approximated to a linear expression. Also, the asterisk "*" indicates a substance whose negative correlation with eGFR was discovered for the first time.
Figure 50:
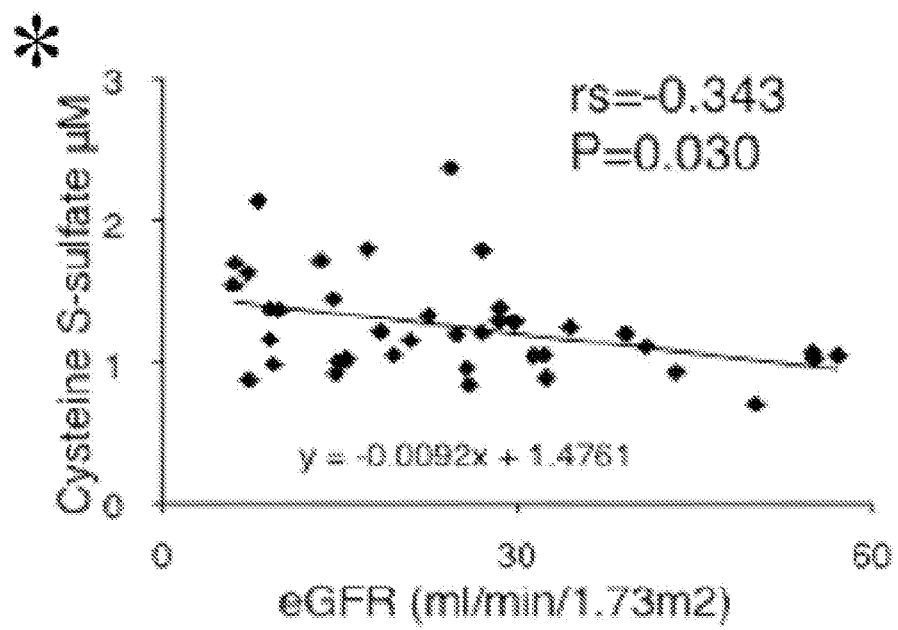
FIG. 50 is a graph showing the correlation between the concentration of an anion found to be negatively correlated with eGFR and eGFR. The correlation was approximated to a linear expression. Also, the asterisk "*" indicates a substance whose negative correlation with eGFR was discovered for the first time.
Figure 51:
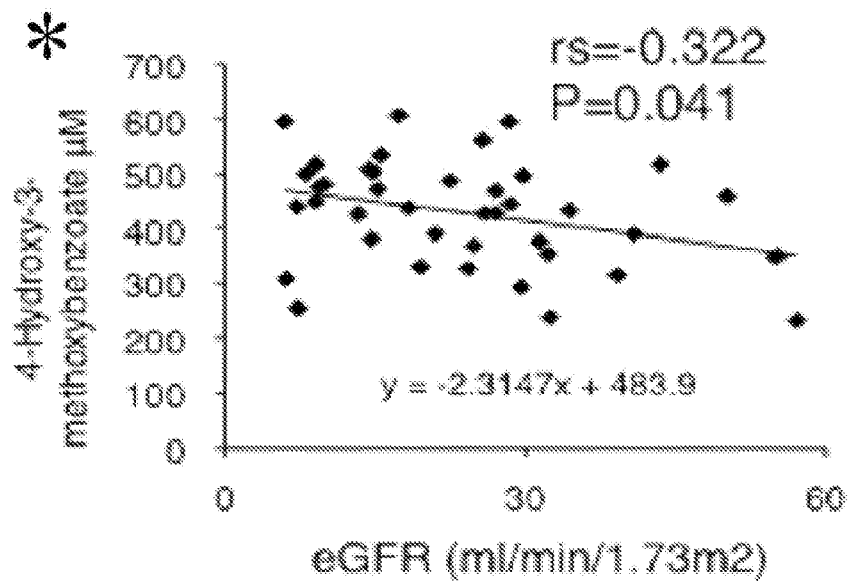
FIG. 51 is a graph showing the correlation between the concentration of an anion found to be negatively correlated with eGFR and eGFR. The correlation was approximated to a linear expression. Also, the asterisk "*" indicates a substance whose negative correlation with eGFR was discovered for the first time.
Figure 52:
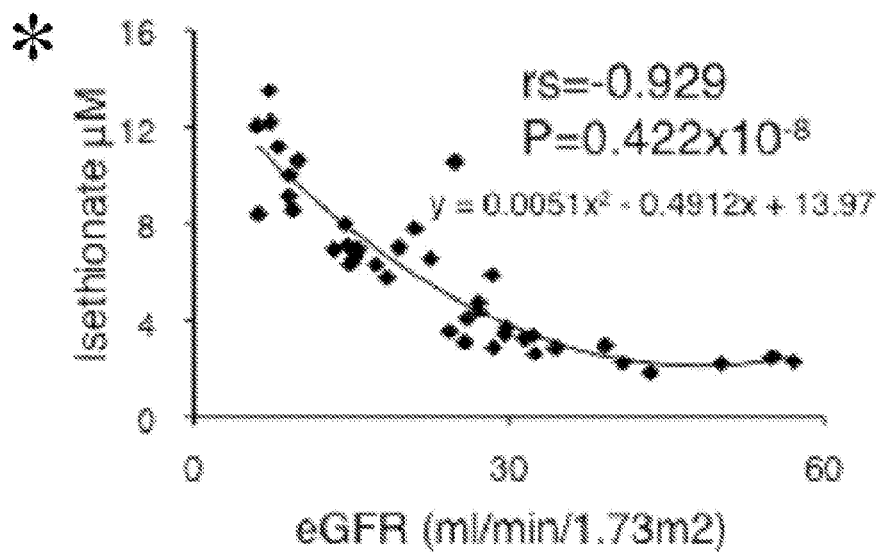
FIG. 52 is a graph showing the correlation between the concentration of an anion found to be negatively correlated with eGFR and eGFR. The correlation was approximated to a quadratic equation. Also, the asterisk "*" indicates a substance whose negative correlation with eGFR was discovered for the first time.
Figure 53:
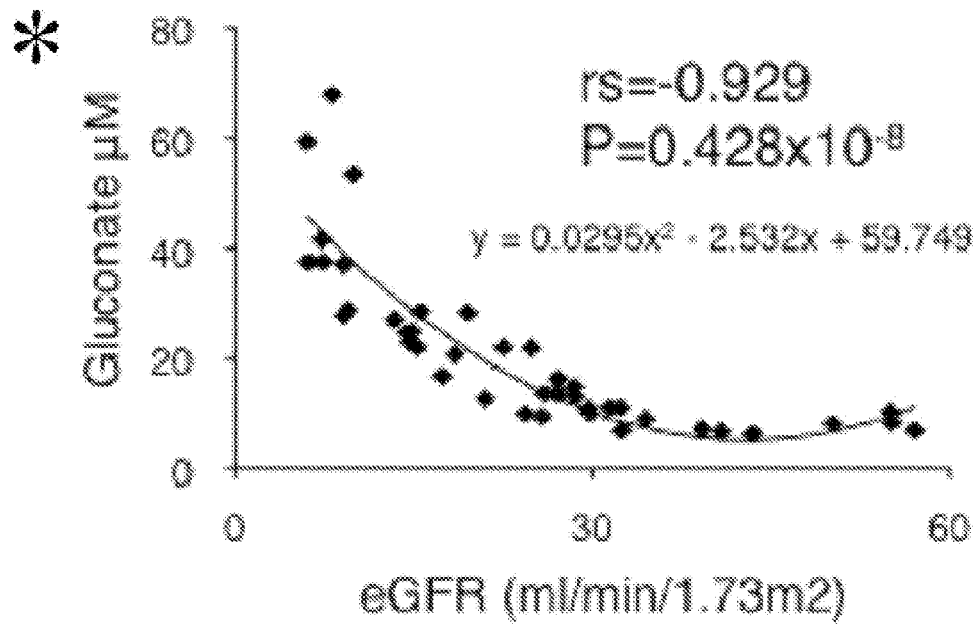
FIG. 53 is a graph showing the correlation between the concentration of an anion found to be negatively correlated with eGFR and eGFR. The correlation was approximated to a quadratic equation. Also, the asterisk "*" indicates a substance whose negative correlation with eGFR was discovered for the first time.
Figure 54:
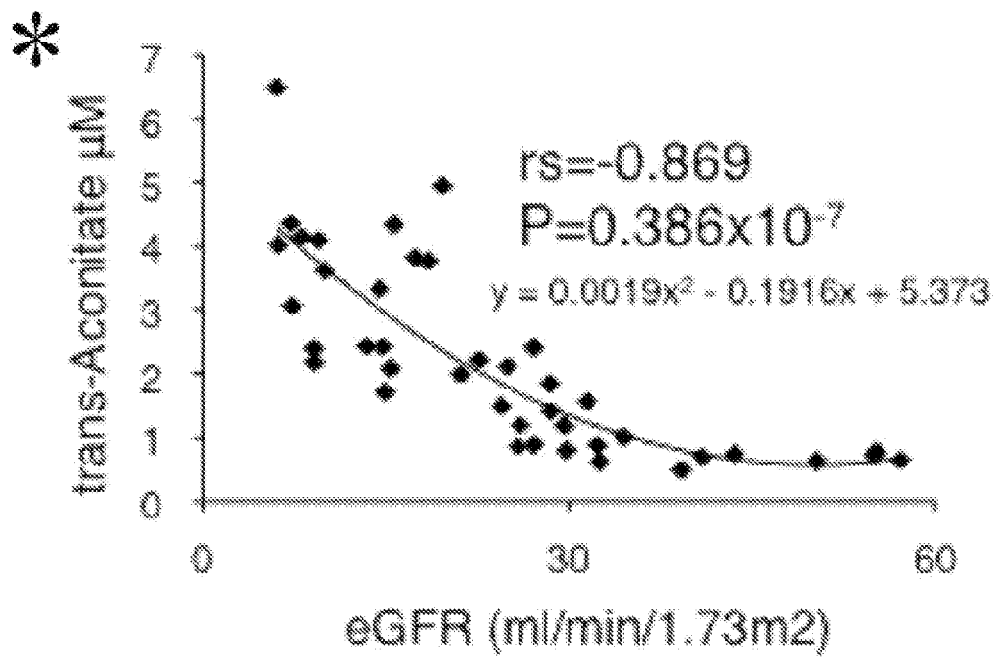
FIG. 54 is a graph showing the correlation between the concentration of an anion found to be negatively correlated with eGFR and eGFR. The correlation was approximated to a quadratic equation. Also, the asterisk "*" indicates a substance whose negative correlation with eGFR was discovered for the first time.
Figure 55:
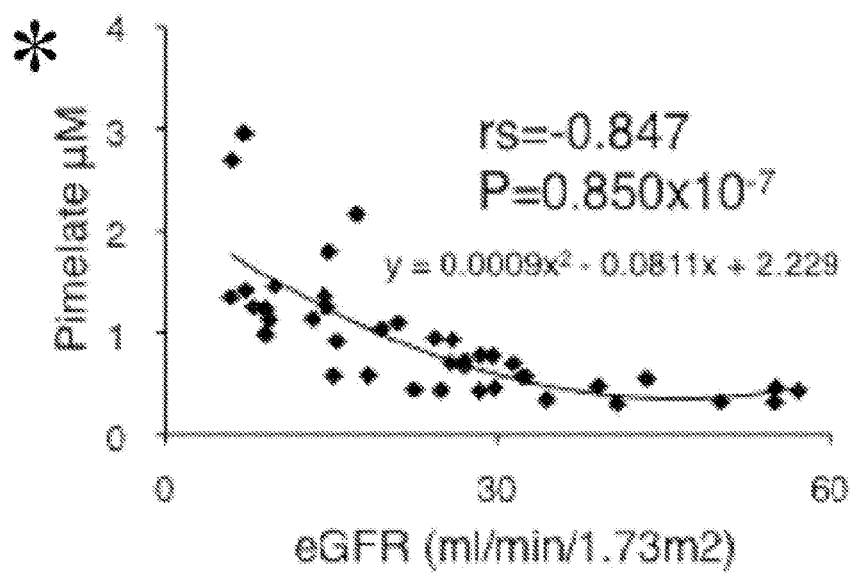
FIG. 55 is a graph showing the correlation between the concentration of an anion found to be negatively correlated with eGFR and eGFR. The correlation was approximated to a quadratic equation. Also, the asterisk "*" indicates a substance whose negative correlation with eGFR was discovered for the first time.
Figure 56:
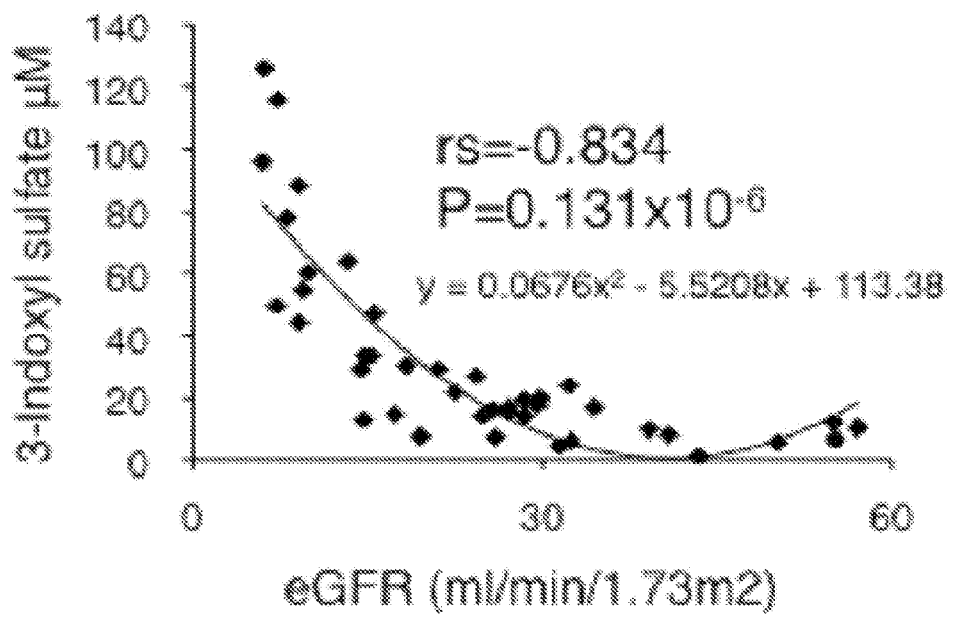
FIG. 56 is a graph showing the correlation between the concentration of an anion found to be negatively correlated with eGFR and eGFR. The correlation was approximated to a quadratic equation.
Figure 57:
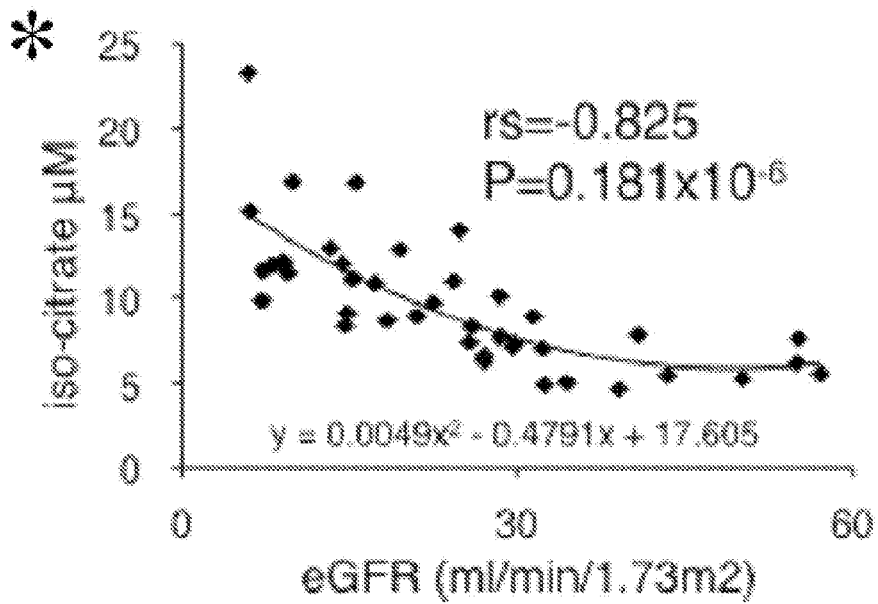
FIG. 57 is a graph showing the correlation between the concentration of an anion found to be negatively correlated with eGFR and eGFR. The correlation was approximated to a quadratic equation. Also, the asterisk "*" indicates a substance whose negative correlation with eGFR was discovered for the first time.
Figure 58:
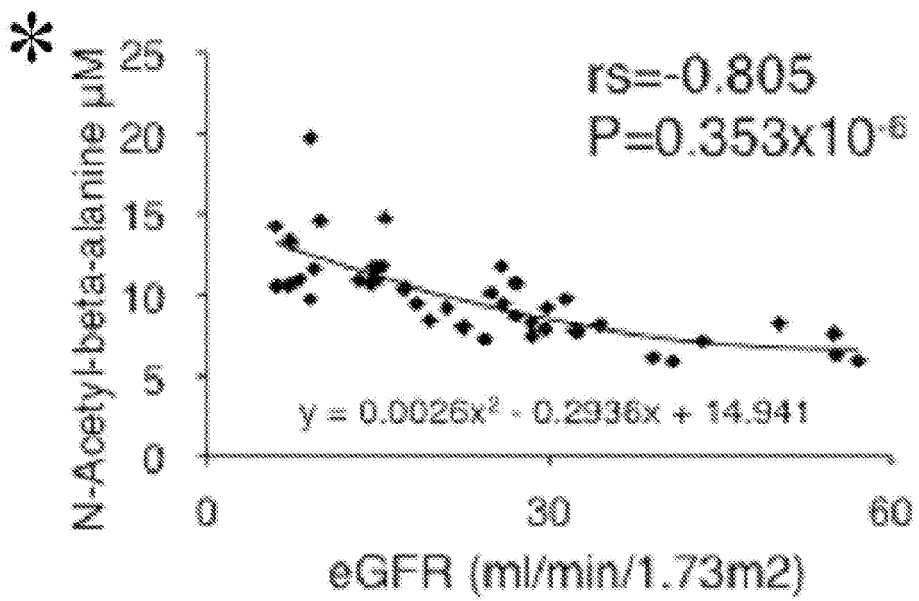
FIG. 58 is a graph showing the correlation between the concentration of an anion found to be negatively correlated with eGFR and eGFR. The correlation was approximated to a quadratic equation. Also, the asterisk "*" indicates a substance whose negative correlation with eGFR was discovered for the first time.
Figure 59:
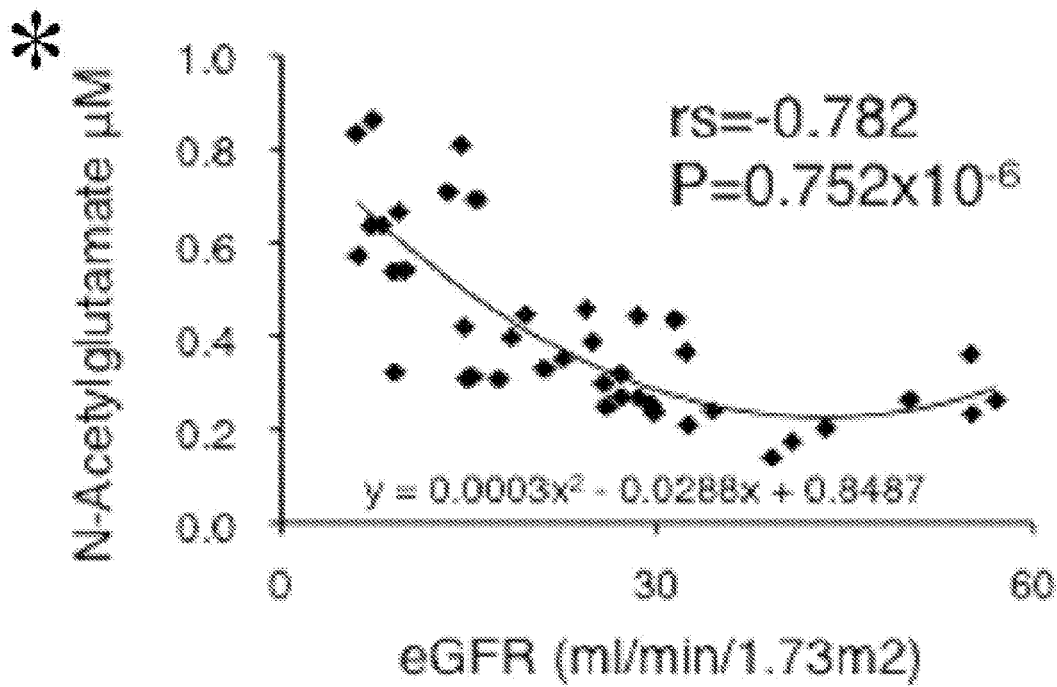
FIG. 59 is a graph showing the correlation between the concentration of an anion found to be negatively correlated with eGFR and eGFR. The correlation was approximated to a quadratic equation. Also, the asterisk "*" indicates a substance whose negative correlation with eGFR was discovered for the first time.
Figure 60:
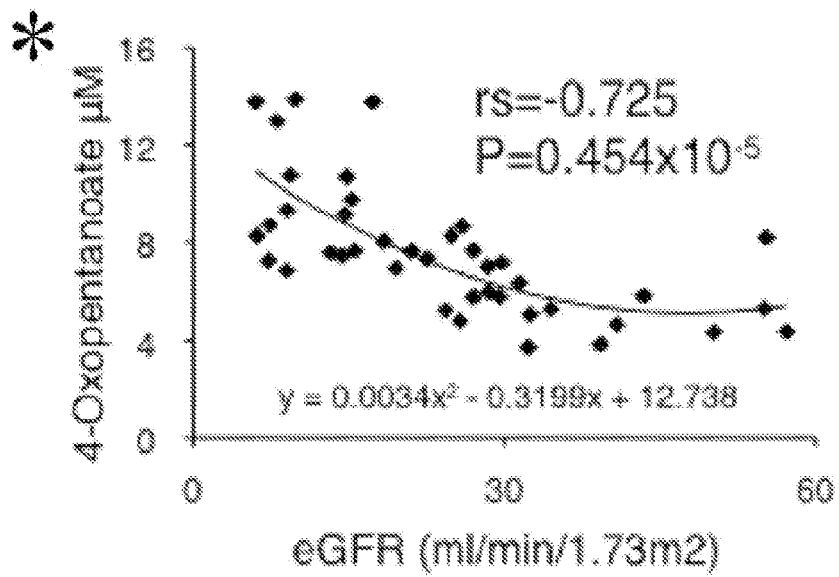
FIG. 60 is a graph showing the correlation between the concentration of an anion found to be negatively correlated with eGFR and eGFR. The correlation was approximated to a quadratic equation. Also, the asterisk "*" indicates a substance whose negative correlation with eGFR was discovered for the first time.
Figure 61:
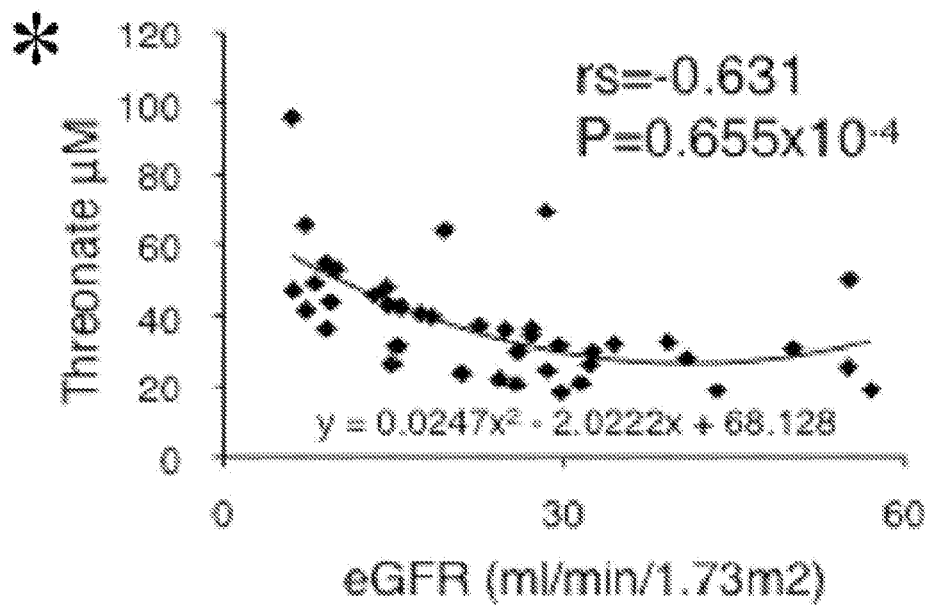
FIG. 61 is a graph showing the correlation between the concentration of an anion found to be negatively correlated with eGFR and eGFR. The correlation was approximated to a quadratic equation. Also, the asterisk "*" indicates a substance whose negative correlation with eGFR was discovered for the first time.
Figure 62:
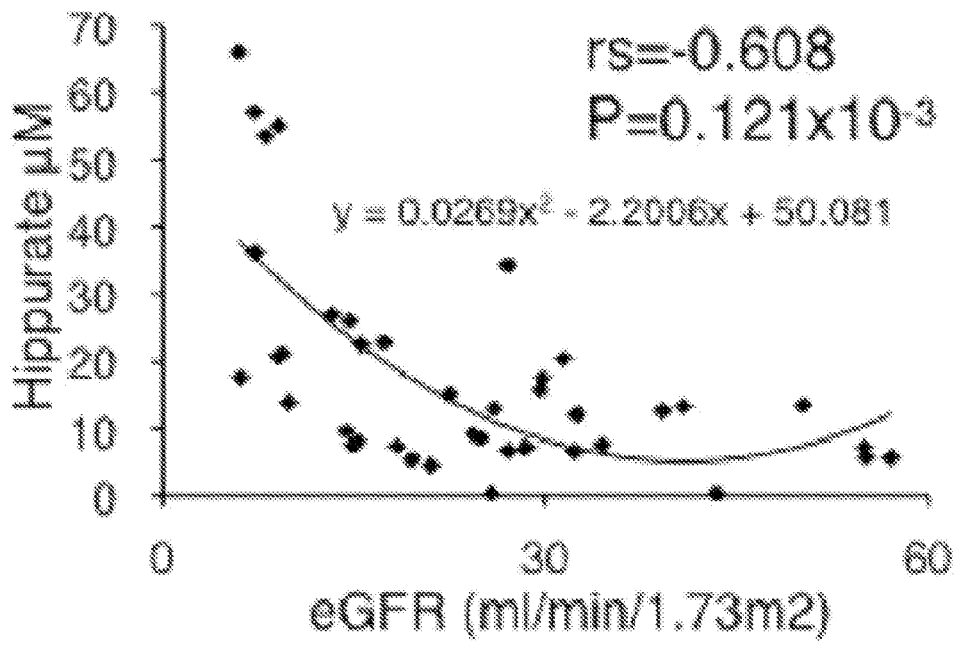
FIG. 62 is a graph showing the correlation between the concentration of an anion found to be negatively correlated with eGFR and eGFR. The correlation was approximated to a quadratic equation.
Figure 63:
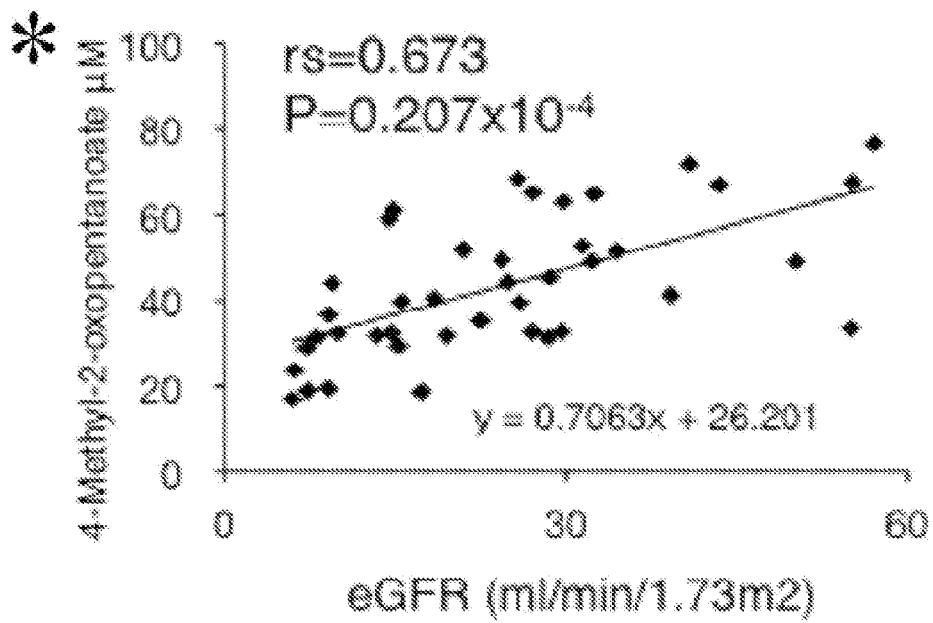
FIG. 63 is a graph showing the correlation between the concentration of an anion found to be positively correlated with eGFR and eGFR. The correlation was approximated to a linear expression. Also, the asterisk "*" indicates a substance whose negative correlation with eGFR was discovered for the first time.
Figure 64:
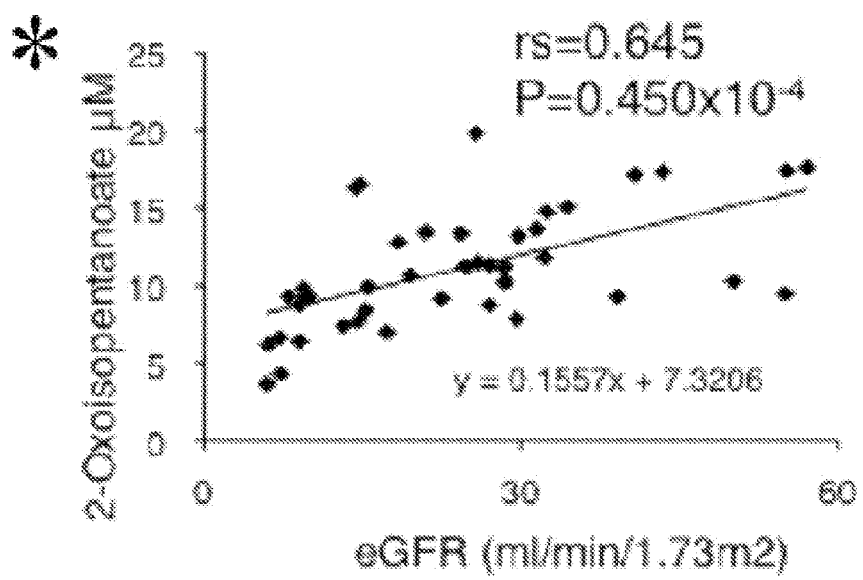
FIG. 64 is a graph showing the correlation between the concentration of an anion found to be positively correlated with eGFR and eGFR. The correlation was approximated to a linear expression. Also, the asterisk "*" indicates a substance whose negative correlation with eGFR was discovered for the first time.
Figure 65:
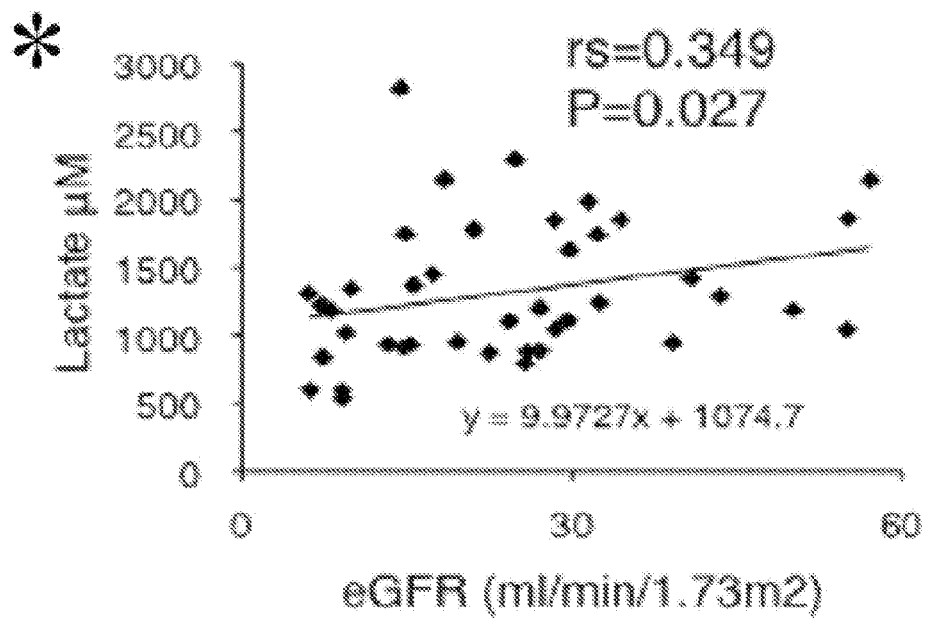
FIG. 65 is a graph showing the correlation between the concentration of an anion found to be positively correlated with eGFR and eGFR. The correlation was approximated to a linear expression. Also, the asterisk "*" indicates a substance whose negative correlation with eGFR was discovered for the first time.
Figure 66:
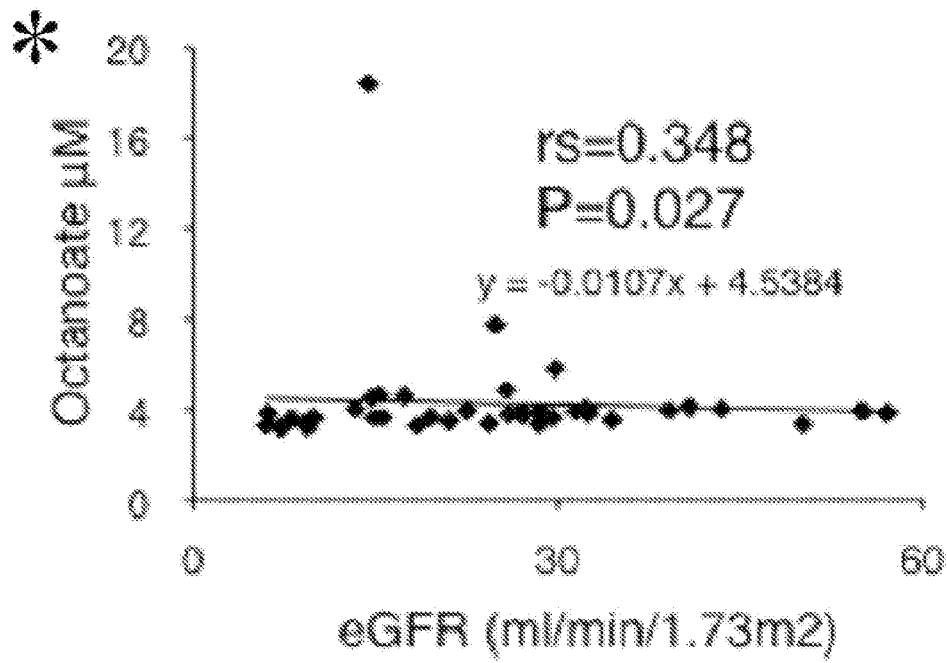
FIG. 66 is a graph showing the correlation between the concentration of an anion found to be positively correlated with eGFR and eGFR. The correlation was approximated to a linear expression. Also, the asterisk "*" indicates a substance whose negative correlation with eGFR was discovered for the first time.

Also, the currently used renal failure marker substances including creatinine have many deficiencies such as being a marker mainly indicating the glomerular filtration rate and requiring the calculation of eGFR. However, among the present renal disease marker substances, 31 kinds of the renal disease marker substances, namely N-acetylglucosamine (FIG. 5), γ-butyrobetaine (FIG. 6), N-ε-acetyllysine (FIG. 11), hypotaurine (FIG. 14), 7-methylguanine (FIG. 16), methionine sulfoxide (FIG. 17), asparagine (FIG. 18), 2-aminobutyrate (FIG. 27), glutamic acid (FIG. 29), sebacate (FIG. 33), cis-aconitate (FIG. 34), homovanillate (FIG. 35), adipate (FIG. 36), citramalate (FIG. 37), 2-isopropylmalate (FIG. 38), N-acetylaspartate (FIG. 39), 4-hydroxy-3-methoxymandelate (FIG. 40), oxamate (FIG. 41), glutarate (FIG. 42), azetate (FIG. 43), phthalate (FIG. 44), malonate (FIG. 46), citraconate (FIG. 47), quinate (FIG. 48), succinate (FIG. 49), cysteine S-sulfate (FIG. 50), 4-hydroxy-3-methoxybenzoate (FIG. 51), 4-methyl-2-oxopentanoate (FIG. 63), 2-oxoisopentanoate (FIG. 64), lactate (FIG. 65), and octanoate (FIG. 66) have correlation equations for eGFR that approximate to a linear equation, and thus can be used for determination of a renal disease without requiring complicated calculation formulas for eGFR of a subject (a donor of a test blood sample). For this, they can be preferably used as more convenient renal disease marker substances. Also, the aforementioned 31 kinds of renal disease marker substances are considered to be preferably applicable for determination and detection of an early stage renal disease.

Also, among the present renal disease marker substances described above, examples of the present renal disease marker substance whose concentration increases with a deterioration in renal function (substances that significantly accumulate in blood with a reduction in eGFR) can include a group of cations consisting of N-acetylglucosamine, γ-butyrobetaine, ophthalmate, N-ε-acetyllysine, cytosine, hypotaurine, 7-methylguanine, methionine sulfoxide, and asparagine and a group of anions consisting of isethionate, gluconate, trans-aconitate, pimelate, isocitrate, N-acetyl-β-alanine, N-acetylglutamate, sebacate, 4-oxopentanoate, cis-aconitate, homovanillate, adipate, citramalate, 2-isopropylmalate, threonate, N-acetylaspartate, 4-hydroxy-3-methoxymandelate, oxamate, glutarate, azetate, phthalate, malonate, citraconate, quinate, succinate, cysteine S-sulfate, and 4-hydroxy-3-methoxybenzoate. Also, examples of the present renal disease marker substance whose concentration decreases with a deterioration in renal function (substances whose blood levels significantly decrease with a reduction in eGFR) can include a group of cations consisting of 2-aminobutyrate and glutamic acid and a group of anions consisting of 4-methyl-2-oxopentanoate, 2-oxoisopentanoate, lactate, octanoate, and 2-oxoglutarate.

Also, among the present renal disease marker substances, even the concentrations of 1-methyladenosine, cis-aconitate, and homovanillate in a group with slightly reduced eGFR (eGFR 30 to 59) were significantly different from those in healthy individuals, and thus these substances can be particularly preferably used for determination and detection of an early stage renal disease or for determination and detection of a renal disease with high sensitivity. Among them, cis-aconitate and homovanillate, of which particularly cis-aconitate exists at a very low concentration in healthy individuals, and thus is a particularly excellent renal disease marker for determination and detection of an early stage renal disease or for determination and detection of a renal disease with high sensitivity.

Also, the aforementioned test blood sample is not particularly limited as long as it is a sample derived from blood of a subject (a donor of a test blood sample), and it may be a blood sample per se or a serum or plasma sample obtained from the blood sample. However, from the viewpoint of achieving higher accuracy of the detection and quantification, preferable examples of the test blood sample include a plasma sample.

The method for detecting or quantifying the aforementioned present renal disease marker substance may be either a physicochemical method or a biological method as long as it can detect or quantify the present renal disease marker substance; however, the method is preferably exemplified by a physicochemical method in terms of detection sensitivity. Among the physicochemical methods, preferred examples include methods using a mass spectrometer (MS) such as a liquid chromatograph mass spectrometer (LC/MS), a gas chromatograph mass spectrometer (GC/MS), and a capillary electrophoresis mass spectrometer (CE-MS). The method is particularly preferably exemplified by a method using CE-MS since it enables simultaneous measurement of several hundred or more kinds of substances from a small amount of sample.

The method for determining a renal disease of the present invention preferably further including the step of comparing the result of detection or quantification of the present renal disease marker substance with that of a control to determine whether a donor of the test blood sample has a renal disease or evaluate a degree of symptoms of a renal disease of the donor. Preferred examples of the aforementioned control include the results of detection or quantification (preferably, the "standard value" to be described later) of the present renal disease marker substance in a blood sample (more preferably the same type of blood sample as the test blood sample) obtained from patients without a renal disease (preferably healthy individuals). For example, the amount of the present renal disease marker substance in a test blood sample quantified by the aforementioned method is converted into concentration, and the concentration thus obtained is compared with a standard value that is determined based on the concentration of the present renal disease marker substance in a test blood sample obtained from patients without a renal disease, whereby it can be determined whether the donor of the test blood sample has a renal disease. Here, the "standard value" refers to a value used for determining if the sample is positive or negative. For example, in the case of the present renal disease marker substance whose concentration increases with a deterioration in renal function, the standard value can be set by the following mathematical formula; "the average concentration value of a specific present renal disease marker substance in a blood sample of a patient without a renal disease"+(α×standard deviation (SD)), wherein α is 0.5, 1, 2 or 5. In the case of the present renal disease marker substance whose concentration decreases with a deterioration in renal function, the standard value can be set by the following mathematical formula; "the average concentration value of a specific present renal disease marker substance in a blood sample of a patient without a renal disease"−(α×standard deviation (SD)), wherein α is 0.5, 1, 2 or 5. It should be note that in a population with a normal distribution of concentration, a is mostly 2 in either formula.

Specifically, the present renal disease marker substance in the blood sample of a population of patients without a renal disease is quantified and the standard value is set by the aforementioned formulas. When the renal disease marker substance is a substance whose concentration increases with a deterioration in renal function (i.e., N-acetylglucosamine, γ-butyrobetaine, ophthalmate, N-ε-acetyllysine, cytosine, hypotaurine, 7-methylguanine, methionine sulfoxide, asparagine, isethionate, gluconate, trans-aconitate, pimelate, isocitrate, N-acetyl-β-alanine, N-acetylglutamate, sebacate, 4-oxopentanoate, cis-aconitate, homovanillate, adipate, citramalate, 2-isopropylmalate, threonate, N-acetylaspartate, 4-hydroxy-3-methoxymandelate, oxamate, glutarate, azetate, phthalate, malonate, citraconate, quinate, succinate, cysteine S-sulfate, and 4-hydroxy-3-methoxybenzoate), the donor of a test blood sample is identified as positive (suffering from a renal disease) when the renal disease marker substance in the test blood sample exists at a higher concentration than a control (preferably the standard value). Also, the degree of severity of symptoms of a renal disease of the donor can be evaluated to be equivalent to a degree by which the concentration of the aforementioned present renal disease marker substance in the test blood sample exceeds the control.

Meanwhile, when the renal disease marker substance is a substance whose concentration decreases with a deterioration in renal function (i.e., 2-aminobutyrate, glutamic acid, 4-methyl-2-oxopentanoate, 2-oxoisopentanoate, lactate, octanoate, and 2-oxoglutarate), the donor of a test blood sample is identified as positive (suffering from a renal disease) when the renal disease marker substance in the test blood sample exists at a lower concentration than a control (preferably the standard value). Also, the degree of severity of symptoms of a renal disease of the donor can be evaluated to be equivalent to a degree by which the concentration of the aforementioned present renal disease marker substance in the test blood sample falls below the control. It should be noted that the standard value need not be calculated every time the present renal disease marker substance in a blood test sample is detected. For example, if standard values are measured with respect to various kinds of blood samples and calibration curves are prepared for respective blood samples in advance, then such calibration curves can be immediately used by, for example, searching for the standard value of the same type of blood sample as the test blood sample. It is to be noted that when the present renal disease marker substance cannot be detected, the concentration of the substance may be regarded as zero.

Also, the present renal disease marker substance can also be utilized for management of the pathological condition of a renal disease. The pathological condition of a renal disease can be managed by, for example, converting the amount of the present renal disease marker substance in a test blood sample quantified by the aforementioned quantification method into concentration, and then evaluating eGFR from the concentration thus obtained. In the present specification, management of the pathological condition refers to recognition of the severity of the disease state and observation of the prognosis.

Preferred examples of the renal disease that can be determined by or whose pathological condition can be managed by the method for determining a renal disease of the present invention include chronic renal failure, acute renal failure, glomerulonephritis, nephrotic syndrome, nephrosclerosis, immune complex nephropathy, lupus nephritis, diabetic nephropathy, drug-induced renal dysfunction, hypertensive nephropathy, polycystic kidney, and IgA nephropathy, among which more preferred examples include chronic renal failure, acute renal failure, and diabetic nephropathy.

The method for determining an early stage renal disease of the present invention (second embodiment of the present invention)

Examples of the currently used, publicly known renal disease marker substance include creatinine and cystatin C. While the urinary concentrations of these publicly known renal disease marker substances gradually increase with a reduction in GFR, particularly in terminal renal disease, they exhibit abruptly ascending curves which rather resemble a quadratic curve (see FIGS. 68 to 74). Also, the aforementioned publicly known renal disease marker substances have been not suitable for detection of an early stage renal disease because they exhibit a gradual increase in the concentration in an early stage renal disease. Further, a complicated calculation formula has been required also for calculating eGFR from the concentration of the aforementioned publicly known renal disease marker substance. In view of the above, the present inventors conducted more detailed studies on the relationship between eGFR and 64 kinds of renal disease marker substances significantly correlated with eGFR, thereby discovering the marker substances for an early stage renal disease whose correlation with eGFR approximates to a linear equation.

The method for determining an early stage renal disease of the present invention is not particularly limited as long as it is a method for determination including the step of detecting or quantifying one or two or more renal disease marker substances present in a test blood sample, selected from the following renal disease marker substances (hereinbelow, may also be expressed as "the present marker substance for an early stage renal disease").

(Cationic marker substances for an early stage renal disease negatively correlated with eGFR): 1-methyladenosine, N-acetylglucosamine, γ-butyrobetaine, 3-methylhistidine, hydroxyproline, trimethylamine-N-oxide, asymmetric dimethylarginine (ADMA), N-ε-acetyllysine, kynurenine, indole-3-acetate, hypotaurine, N,N-dimethylglycine, 7-methylguanine, methionine sulfoxide, and asparagine;

(Cationic marker substances for an early stage renal disease positively correlated with eGFR): valine, 2-aminobutyrate, guanidoacetate, glutamic acid, and leucine; (Anionic marker substances for an early stage renal disease negatively correlated with eGFR): sebacate, cis-aconitate, homovanillate, adipate, citramalate, 2-isopropylmalate, N-acetylaspartate, 4-hydroxy-3-methoxymandelate, oxamate, glutarate, azetate, phthalate, citrate, malonate, citraconate, quinate, succinate, cysteine S-sulfate, and 4-hydroxy-3-methoxybenzoate; (Anionic marker substances for an early stage renal disease positively correlated with eGFR): 4-methyl-2-oxopentanoate, 2-oxoisopentanoate, lactate and octanoate;

Also, from the viewpoint of further increasing the accuracy of the method for determining an early stage renal disease of the present invention, a method of concomitantly using two or more kinds of the present marker substances for an early stage renal disease is also possible.

Also, among the present marker substances for an early stage renal disease, even the concentrations of 1-methyladenosine, cis-aconitate, and homovanillate in a group with slightly reduced eGFR (eGFR 30 to 59) were significantly different from those in healthy individuals, and thus these marker substances for an early stage renal disease can be particularly preferably used for determination and detection of an early stage renal disease and for determination and detection of a renal disease with high sensitivity. Among them, cis-aconitate and homovanillate, of which particularly cis-aconitate exists at a very low concentration in healthy individuals, and thus can be a particularly excellent renal disease marker for determination and detection of an early stage renal disease and for determination and detection of a renal disease with high sensitivity.

The method for determining an early stage renal disease of the present invention enables determining whether a donor of a test blood sample has an early stage renal disease, or the degree of symptoms of an early stage renal disease of the donor.

Among the present marker substances for an early stage renal disease described above, 1-methyladenosine, 3-methylhistidine, hydroxyproline, trimethylamine-N-oxide, asymmetric dimethylarginine (ADMA), kynurenine, indole-3-acetate, N,N-dimethylglycine, valine, guanidoacetate, leucine, and citrate have been known to be associated with a renal disease; however, the fact that the correlation equations between these substances and eGFR approximate to a linear equation, meaning that these substances can be employed as the marker substance for an early stage renal disease, was revealed for the first time by the present inventors.

The method for screening for a prophylactic/therapeutic agent for a renal disease of the present invention (third embodiment of the present invention)

The method for screening for a prophylactic/therapeutic agent for a renal disease of the present invention is not particularly limited as long as it includes the following steps A) to D): A) administering a test substance to a non-human animal with reduced renal function; B) collecting a blood sample from the non-human animal; C) detecting or quantifying one or two or more renal disease marker substances present in the blood sample, selected from the renal disease marker substances (N-acetylglucosamine, γ-butyrobetaine, ophthalmate, N-ε-acetyllysine, cytosine, hypotaurine, 7-methylguanine, methionine sulfoxide, asparagine, 2-aminobutyrate, glutamic acid, isethionate, gluconate, trans-aconitate, pimelate, isocitrate, N-acetyl-β-alanine, N-acetylglutamate, sebacate, 4-oxopentanoate, cis-aconitate, homovanillate, adipate, citramalate, 2-isopropylmalate, threonate, N-acetylaspartate, 4-hydroxy-3-methoxymandelate, oxamate, glutarate, azetate, phthalate, malonate, citraconate, quinate, succinate, cysteine S-sulfate, 4-hydroxy-3-methoxybenzoate, 4-methyl-2-oxopentanoate, 2-oxoisopentanoate, lactate, octanoate, and 2-oxoglutarate); and D) comparing the result of detection or quantification of the renal disease marker substance present in the blood sample with that of a control to evaluate renal function of the non-human animal. However, the aforementioned step D preferably includes a step D' to determine the aforementioned test substance as a prophylactic/therapeutic agent for a renal disease when the present renal disease marker substance whose concentration increases with a deterioration in renal function exists at a lower concentration than that of a control, or when the present renal disease marker substance whose concentration decreases with a deterioration in renal function exists at a higher concentration than that of a control.

Preferred examples of the aforementioned non-human animal include non-human mammals, of which preferred examples include mice, rats, hamsters, guinea pigs, monkeys, cows, pigs, horses, rabbits, sheep, goats, cats, and dogs.

EXAMPLES

Example 1

Background of Patients with a Renal Disease

Plasma samples for CE-MS analysis to be described later were obtained from 41 patients with a chronic renal disease receiving outpatient treatment at Tohoku University Hospital. It should be noted that this research program was approved by the Medical Ethics Committee of Tohoku University in advance and informed consent was obtained from each patient before collection of the plasma sample. The background of these patients was as follows; an average age was 62.9±14.6, and among patients, there were 26 males and 15 females. An average estimated glomerular filtration rate (eGFR) of these patients was calculated as 24.4±13.9 ml/min/1.73 m$^2$ by the estimation formula recommended by Japanese Society of Nephrology, and all the patients were classified as having a value below the standard for the diagnosis of chronic renal failure (CKD), which is 60 ml/min/1.73 m$^2$. It is to be noted that the aforementioned estimation formula for calculation of eGFR is "eGFR=194×[age]$^{-0.287}$×[blood creatinine (mg/dl)]$^{-1.094}$" for male, and "eGFR=194×[age]$^{-0.287}$×[blood creatinine (mg/dl)]$^{-1.094}$×[0.739]" for female. The background of the 41 patients with a chronic renal disease is shown in FIG. 1.

As shown in FIG. 1, the cause of the chronic renal disease (primary disease) in these patients was as follows; Alport syndrome, one patient (2.4%), allergic nephropathy, one patient (2.4%), ANCA related nephropathy, one patient (2.4%), aortitis syndrome, one patient (2.4%), bilateral renal infarction, one patient (2.4%), diabetic nephropathy, eight patients (19.5%), focal segmental glomerulosclerosis, three patients (7.3%), glomeruloscrelosis, four patients (9.7%), hydronephrosis, one patient (2.4%), IgA nephropathy, nine patients (21.9%), lipoprotein glomerulopathy, one patient (2.4%), lupus nephropathy, two patients (4.8%), membrane proliferative glomerulonephritis, one patient (2.4%), membranous nephropathy, two patients (4.8%), polycystic kidney, one patient (2.4%), primary renal disease, two patients (4.8%), renal tuberculosis, one patient (2.4%), and sarcoidosis, one patient (2.4%). Also, as the underlying disease of these patients, 10 patients had cardiovascular disease, 12 patients had diabetes, and 40 patients had hypertension. Further, among those 41 patients, 11 patients were smokers. As to the kind of oral drugs these patients were taking, 12 patients were taking allopurinol (29.2%), 30 patients were taking angiotensin receptor blockers (73.1%), five patients were taking AST-120 (12.1%), six patients were taking erythropoietin (14.6%), and eight patients were taking statin (19.5%).

Example 2

Analysis of Substances in the Plasma of Patients with a Renal Disease

The present inventors comprehensively analyzed the substances in the plasma samples of all patients with a renal disease collected in Example 1 by CE-MS. Specifically, it was conducted by the following method.

A methanol solution having the adjusted internal standard substance was added to each plasma sample obtained in Example 1, followed by stirring. Chloroform was further added, and the resulting mixture was stirred and centrifuged at 4600 g for five minutes. The supernatant was then collected in an ultrafiltration filter (molecular weight cut off of 5000) and centrifuged at 4° C. and 9100 g for two hours. The filtrate thus obtained was subjected to centrifugal concentration and measured by CE-TOFMS. At this time, 312 kinds of cations and 193 kinds of anions were simultaneously measured in a comprehensive manner. As a result, 66 kinds of cations and 50 kinds of anions were detected in the plasma of the patients with chronic renal failure. The molecular weight of the substances thus detected (hereinbelow, expressed as the "detected substance") was between 73.0 m/z and 460.1 m/z. In order to search for a substance which accumulates in renal failure from among the detected substances, the present inventors analyzed the correlation between the detected substances and eGFR by the Spearman's rank order correlation test. Among the detected substances, the results of cations are shown in FIG. 2 and the results of anions are shown in FIG. 3. Also, FIG. 2 and FIG. 3 each show the results in descending order of correlation coefficient from the top. Among these detected substances, the substance having a P value of 0.05 or less with respect to the correlation was regarded as significantly correlated with eGFR. The present inventors further conducted an analysis and identified, from among the anions and cations significantly correlated with eGFR, a total of 65 kinds of substances, which included 30 kinds of substances that significantly accumulate with a reduction in eGFR and 35 kinds of substances that significantly decrease with a reduction in eGFR.

As shown in FIG. 2, as the cationic substance that significantly accumulates with a reduction in eGFR, creatinine, symmetric dimethylarginine (SDMA), guanidino succinate, citrulline, 1-methyladenosine, N-acetylgulusosamine, γ-butyrobetaine, ophthalmate, 3-methylhistidine, hydroxyproline, trimethylamine N-oxide, allantoin, asymmetric dimethylarginine (ADMA), N-ε-acetyllysine, kynurenine, cytosine, indole-3-acetate, hypotaurine, N,N-dimethylglycine, 7-methylguanine, methionine sulfoxide, and asparagine (Asn) were identified. Also, as shown in FIG. 2, as the cationic substance that significantly decreases with a reduction in eGFR, tryptophan (Trp), valine (Val), tyrosine (Tyr), 2-aminobutyrate, guanidoacetate, glutamic acid (Glu), and leucine (Leu) were identified.

Meanwhile, as shown in FIG. 3, as the anionic substance that significantly accumulates with a reduction in eGFR, isethionate, gluconate, trans-aconitate, pimelate, 3-indoxylsulfate, isocitrate, N-acetyl-β-alanine, N-acetylglutamate, sebacate, 4-oxopentanoate, cis-aconitate, homovanillate, adipate, citramalate, 2-isopropylmalate, threonate, hippurate, N-acetylaspartate, 4-hydroxy-3-methoxymandelate, oxamate, glutarate, azetate, phthalate, citrate, malonate, citraconate, quinate, succinate, cysteine S-sulfate, and 4-hydroxy-3-methoxybenzoate were identified.

Also, as shown in FIG. 3, as the anionic substance that significantly decreases with a reduction in eGFR, 4-methyl-2-oxopentanoate, 2-oxoisopentanoate, lactate, octanoate, pyruvate, and 2-oxoglutarate were identified.

Among these 64 kinds of substances observed to be significantly correlated with eGFR (cations and anions), correlation with renal failure has been reported for some of them including creatinine thus far. Among these 64 kinds of substances, the names of a total of 43 kinds of substances (11 kinds of cations and 32 kinds of anions) having newly discovered, significant correlation with eGFR are shown with a gray background in FIG. 2 or 3. For example, among the cationic substances that significantly accumulate with a reduction in eGFR, N-acetylglucosamine, γ-butyrobetaine, ophthalmate, N-ε-acetyllysine, cytosine, hypotaurine, 7-methylguanine, methionine sulfoxide, and asparagine (Asn) were found to be correlated with renal failure for the first time by the present study.

Also, among the cationic substances that significantly decrease with a reduction in eGFR, 2-aminobutyrate and glutamic acid (Glu) were found to be correlated with renal failure for the first time by the present study.

Meanwhile, most of the anionic substances that significantly accumulate with a reduction in eGFR were found to be correlated with renal failure for the first time by the present study. Specifically, isethionate, gluconate, trans-aconitate, pimelate, isocitrate, N-acetyl-β-alanine, N-acetylglutamate, sebacate, 4-oxopentanoate, cis-aconitate, homovanillate, adipate, citramalate, 2-isopropylmalate, threonate, N-acetylaspartate, 4-hydroxy-3-methoxymandelate, oxamate, glutarate, azetate, phthalate, malonate, citraconate, quinate, succinate, cysteine S-sulfate, and 4-hydroxy-3-methoxybenzoate were found to be correlated with renal failure for the first time by the present study.

Also, among the anionic substances that significantly decrease with a reduction in eGFR, 4-methyl-2-oxopentanoate, 2-oxoisopentanoate, lactate, octanoate, and 2-oxoglutarate were found to be correlated with renal failure for the first time by the present study.

As described above, a total of 43 kinds of these substances significantly correlated with a reduction in eGFR were newly shown to be applicable as the renal disease marker substance.

Example 3

Search for a Marker Substance for an Early Stage Renal Disease

Examples of the currently used, publicly known renal disease marker substance include creatinine and cystatin C. While the urinary concentrations of these publicly known renal disease marker substances gradually increase with a reduction in GFR, particularly in terminal renal disease, they exhibit abruptly ascending curves which rather resemble a quadratic curve. Also, the aforementioned publicly known renal disease marker substances have been not suitable for detection of an early stage renal disease because they exhibit a gradual increase in the concentration in an early stage renal disease. Further, a complicated calculation formula has been required also for calculating eGFR from the concentration of the aforementioned publicly known renal disease marker substance. In view of the above, the present inventors conducted more detailed studies on the relationship between the 64 kinds of renal disease marker substances that were found to be significantly correlated with eGFR in Example 2 with eGFR in an attempt to select a renal disease marker substance capable of detecting a renal disease such as renal failure at an earlier stage and a renal disease marker substance that enables easier calculation of eGFR.

Figure 4:
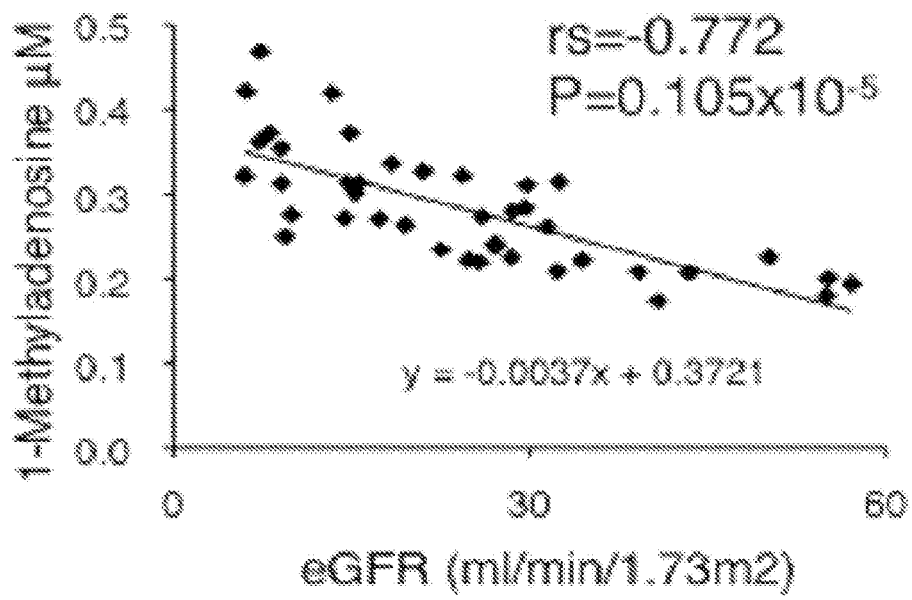
FIG. 4 is a graph showing the correlation between the concentration of a cation found to be negatively correlated with eGFR and eGFR. The correlation was approximated to a linear equation.
Figure 67:
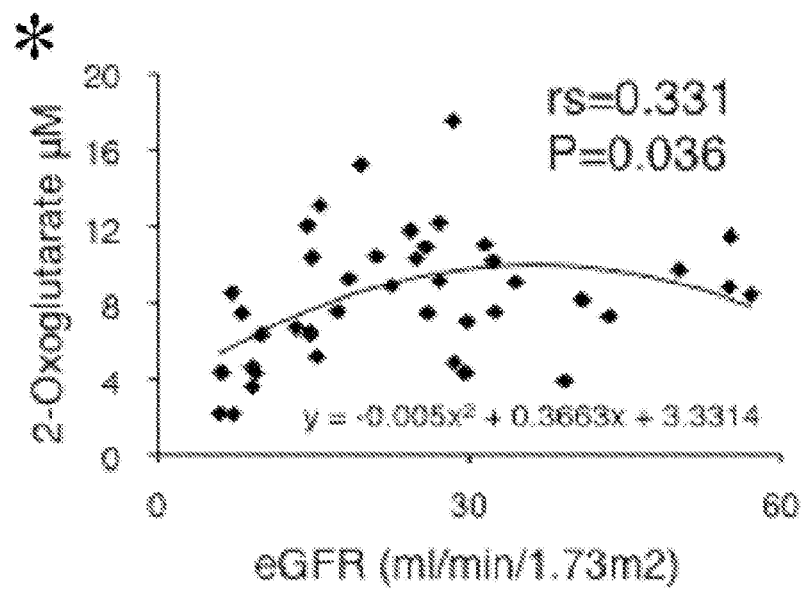
FIG. 67 is a graph showing the correlation between the concentration of an anion found to be positively correlated with eGFR and eGFR. The correlation was approximated to a quadratic expression. Also, the asterisk "*" indicates a substance whose negative correlation with eGFR was discovered for the first time.

Specifically, the present inventors prepared a graph for each of the 64 kinds of renal disease marker substances discovered in Example 2, with the value of eGFR plotted on the horizontal axis and the plasma concentration of the renal disease marker substance plotted on the vertical axis (FIGS. 4 to 67), and selected a renal disease marker substance which has a high Spearman's correlation coefficient between its plasma concentration and eGFR and which increases or decreases in such a way as to approximate to its linear correlation equation. Also, in the case of a renal disease marker substance exhibiting a change that approximates to a linear equation, its correlation with eGFR is expressed as $\ln(Cp)=\beta 1\ (eGFR)+\alpha$, wherein $\ln(Cp)$ indicates the plasma concentration of the renal disease marker substance. Meanwhile, in the case of a substance that approximates to a quadratic equation such as creatinine and cystatin C, its plasma concentration is expressed as $\ln(Cp)=\beta 1\ (eGFR)^2+\beta 2\ (eGFR)+\alpha$. Here, a log likelihood ratio was calculated by treating $(eGFR)^2$ as an independent variable to evaluate whether the correlation equation approximates more closely to a linear equation or a quadratic equation. As a result, among the 22 kinds of cationic substances that significantly accumulate in the body with a reduction in eGFR (FIGS. 4 to 25), 1-methyladenosine, N-acetylglucosamine, γ-butyrobetaine, 3-methylhistidine, hydroxyproline, trimethylamine N-oxide, asymmetric dimethylarginine (ADMA), N-ε-acetyllysine, kynurenine, indole-3-acetate, hypotaurine, N,N-dimethylglycine, 7-methylguanine, methionine sulfoxide, and asparagine were found to have correlation equations for eGFR that approximate to a linear equation. Also, among the seven kinds of cationic substances that significantly decrease with a reduction in eGFR (FIGS. 26 to 32), valine, 2-aminobutyrate, guanidoacetate, glutamic acid, and leucine were found to have correlation equations for eGFR that approximate to a linear equation. Meanwhile, among the 30 kinds of anionic substances that significantly accumulate with a reduction in eGFR (FIGS. 33 to 62), sebacate, cis-aconitate, homovanillate, adipate, citramalate, 2-isopropylmalate, N-acetylaspartate, 4-hydroxy-3-methoxymandelate, oxamate, glutarate, azetate, phthalate, citrate, malonate, citraconate, quinate, succinate, cysteine S-sulfate, and 4-hydroxy-3-methoxybenzoate were found to have correlation equations for eGFR that approximate to a linear equation. Further, among the five kinds of anionic substances that significantly decrease with a reduction in eGFR (FIGS. 63 to 67), 4-methyl-2-oxopentanoate, 2-oxoisopentanoate, lactate, and octanoate were found to have correlation equations for eGFR that approximate to a linear equation.

From the above findings, 1-methyladenosine, N-acetylglucosamine, γ-butyrobetaine, 3-methylhistidine, hydroxyproline, trimethylamine N-oxide, asymmetric dimethylarginine (ADMA), N-ε-acetyllysine, kynurenine, indole-3-acetate, hypotaurine, N,N-dimethylglycine, 7-methylguanine, methionine sulfoxide, asparagine, valine, 2-aminobutyrate, guanidoacetate, glutamic acid, leucine, sebacate, cis-aconitate, homovanillate, adipate, citramalate, 2-isopropylmalate, N-acetylaspartate, 4-hydroxy-3-methoxymandelate, oxamate, glutarate, azetate, phthalate, citrate, malonate, citraconate, quinate, succinate, cysteine S-sulfate, 4-hydroxy-3-methoxybenzoate, 4-methyl-2-oxopentanoate, 2-oxoisopentanoate, lactate, and octanoate were shown to be the renal disease marker substances whose correlation equations for eGFR approximate to a linear equation. Among the renal disease marker substances, the concentrations of the aforementioned 43 kinds of renal disease marker substances change from the early stage of a renal disease, and then linearly increase in a similar way to a linear equation with progression of a renal disease. Therefore, these 43 kinds of renal disease marker substances are assumed to be marker substances for an early stage renal disease that can be preferably used for determination and detection of an early stage renal disease. It should be noted that, among the marker substances for an early stage renal disease, 1-methyladenosine, 3-methylhistidine, hydroxyproline, trimethylamine N-oxide, asymmetric dimethylarginine (ADMA), kynurenine, indole-3-acetate, N,N-dimethylglycine, valine, guanidoacetate, leucine, and citrate have been known to be associated with a renal disease; however, the fact that the correlation equations between these substances and eGFR approximate to a linear equation, meaning that these substances can be employed as the marker substance for an early stage renal disease, was revealed for the first time by the present inventors. Also, the aforementioned 43 kinds of marker substances for an early stage renal disease can be used for determination of renal disease without requiring a complicated calculation formula for eGFR of a subject (a donor of a test blood sample); therefore, these substances are assumed to be preferably used as more convenient renal disease marker substances.

Example 4

Comparison with Cystatin C

Figure 19:
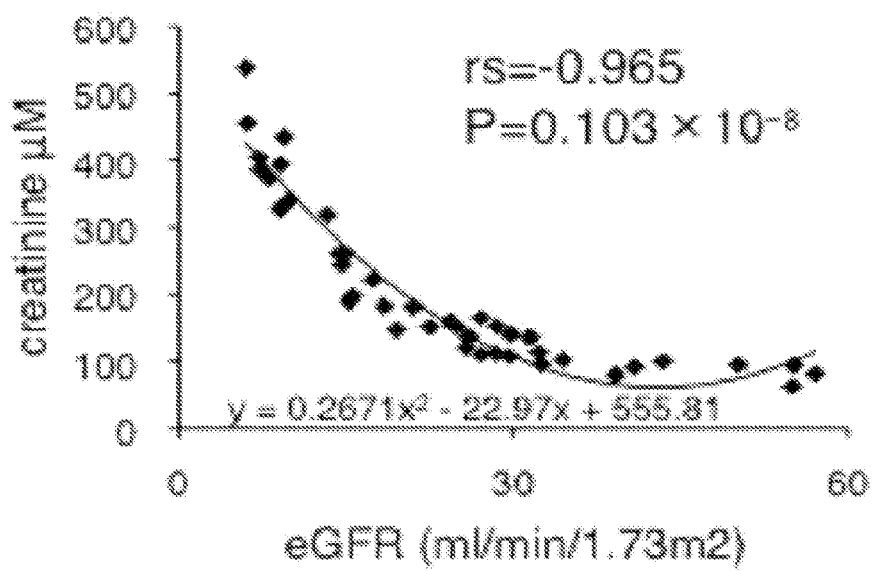
FIG. 19 is a graph showing the correlation between the concentration of a cation found to be negatively correlated with eGFR and eGFR. The correlation was approximated to a quadratic equation.
Figure 20:
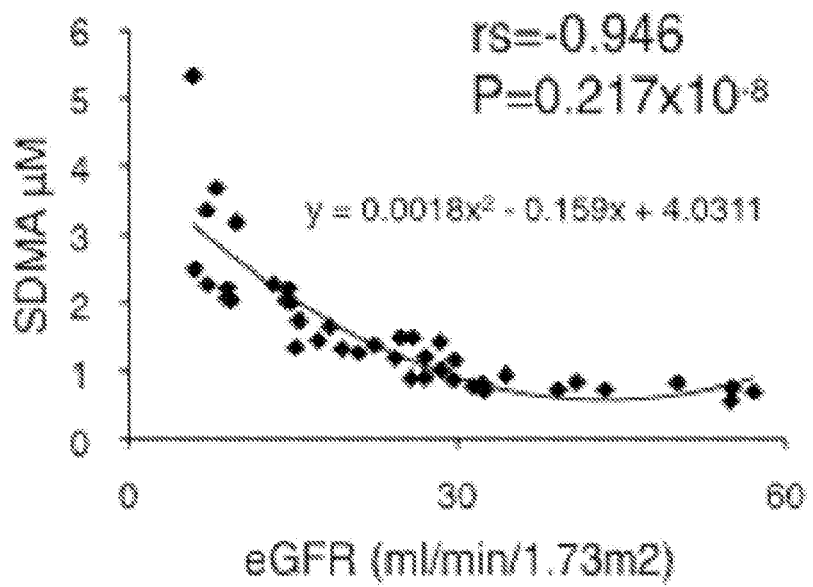
FIG. 20 is a graph showing the correlation between the concentration of a cation found to be negatively correlated with eGFR and eGFR. The correlation was approximated to a quadratic equation.
Figure 21:
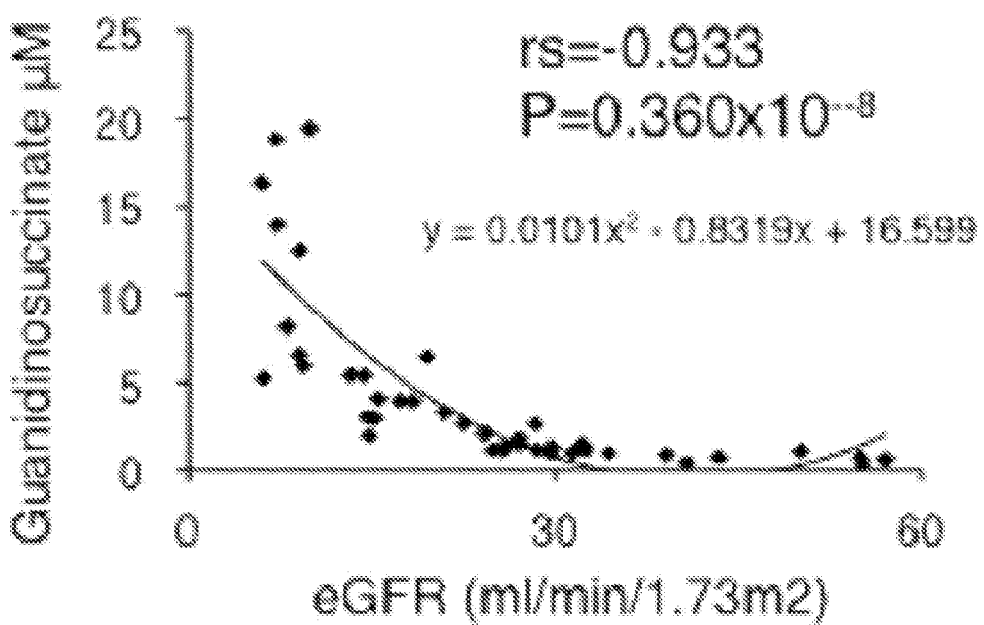
FIG. 21 is a graph showing the correlation between the concentration of a cation found to be negatively correlated with eGFR and eGFR. The correlation was approximated to a quadratic equation.
Figure 22:
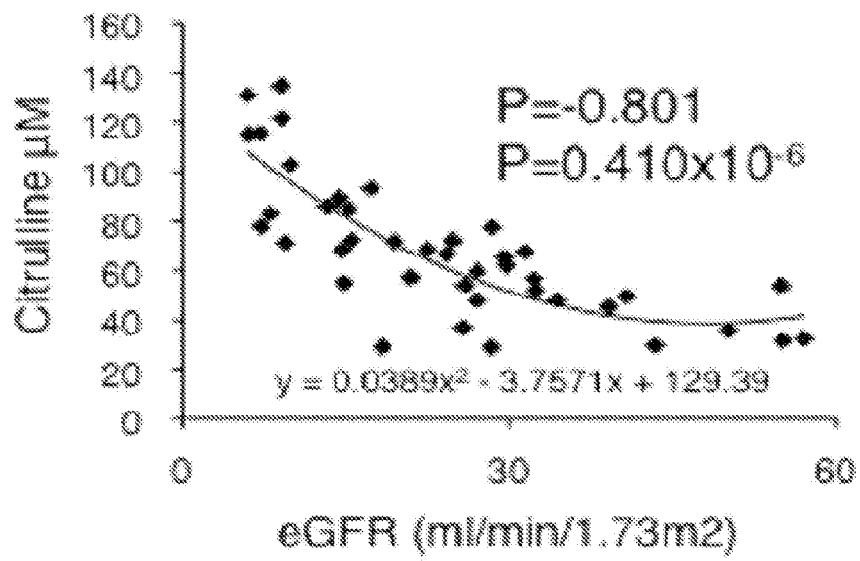
FIG. 22 is a graph showing the correlation between the concentration of a cation found to be negatively correlated with eGFR and eGFR. The correlation was approximated to a quadratic equation.
Figure 23:
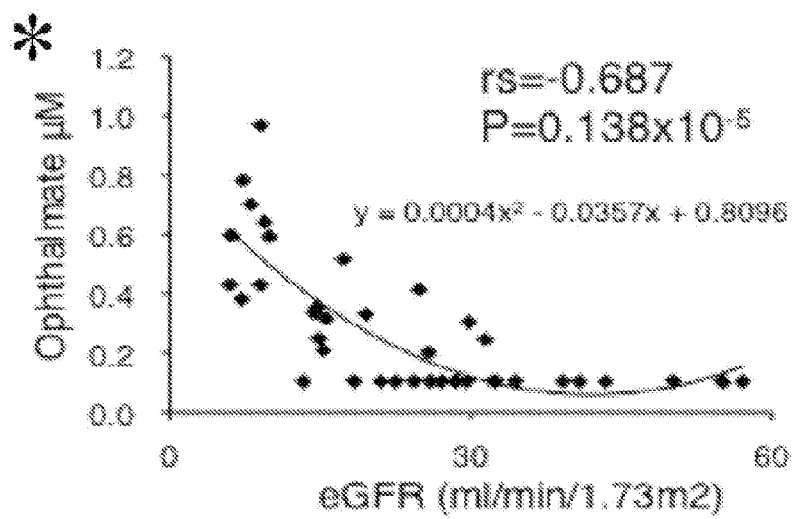
FIG. 23 is a graph showing the correlation between the concentration of a cation found to be negatively correlated with eGFR and eGFR. The correlation was approximated to a quadratic equation. Also, the asterisk "*" indicates a substance whose negative correlation with eGFR was discovered for the first time.
Figure 24:
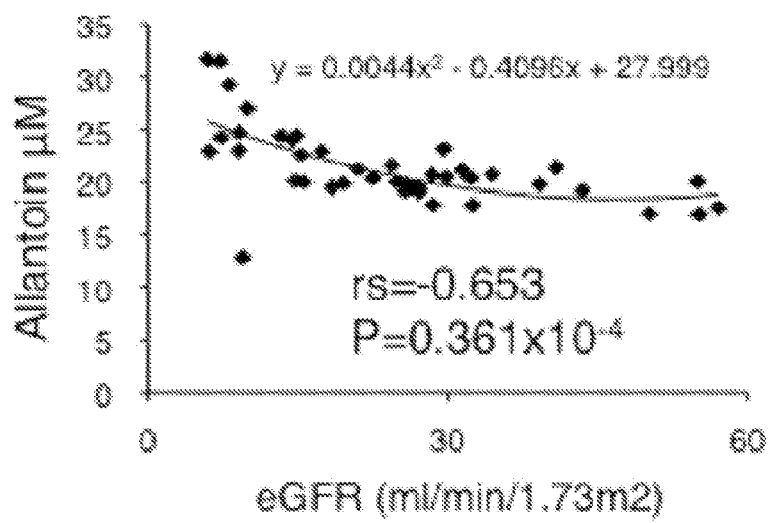
FIG. 24 is a graph showing the correlation between the concentration of a cation found to be negatively correlated with eGFR and eGFR. The correlation was approximated to a quadratic equation.
Figure 25:
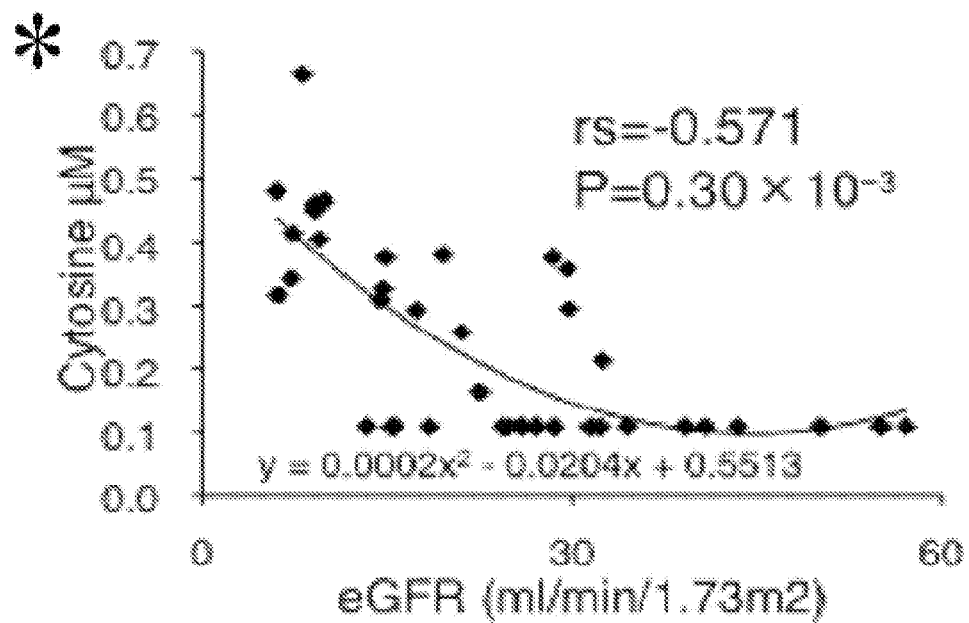
FIG. 25 is a graph showing the correlation between the concentration of a cation found to be negatively correlated with eGFR and eGFR. The correlation was approximated to a quadratic equation. Also, the asterisk "*" indicates a substance whose negative correlation with eGFR was discovered for the first time.
Figure 26:
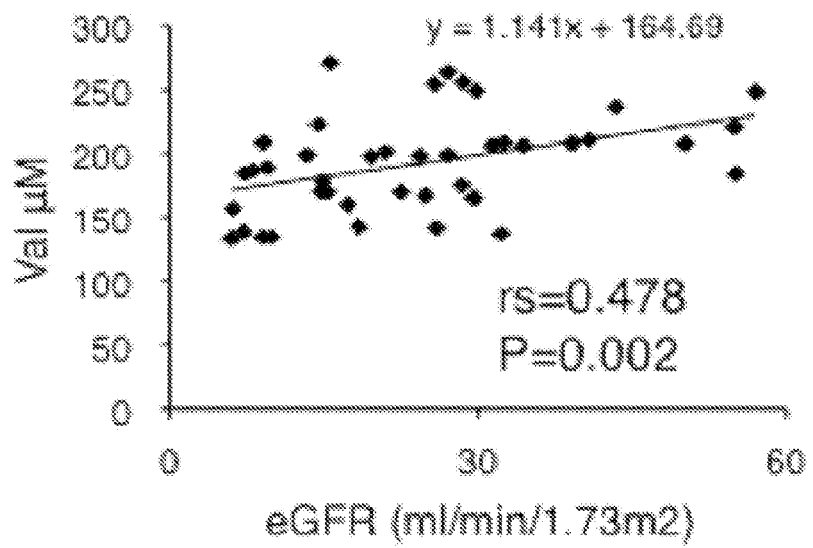
FIG. 26 is a graph showing the correlation between the concentration of a cation found to be positively correlated with eGFR and eGFR. The correlation was approximated to a linear equation.
Figure 68:
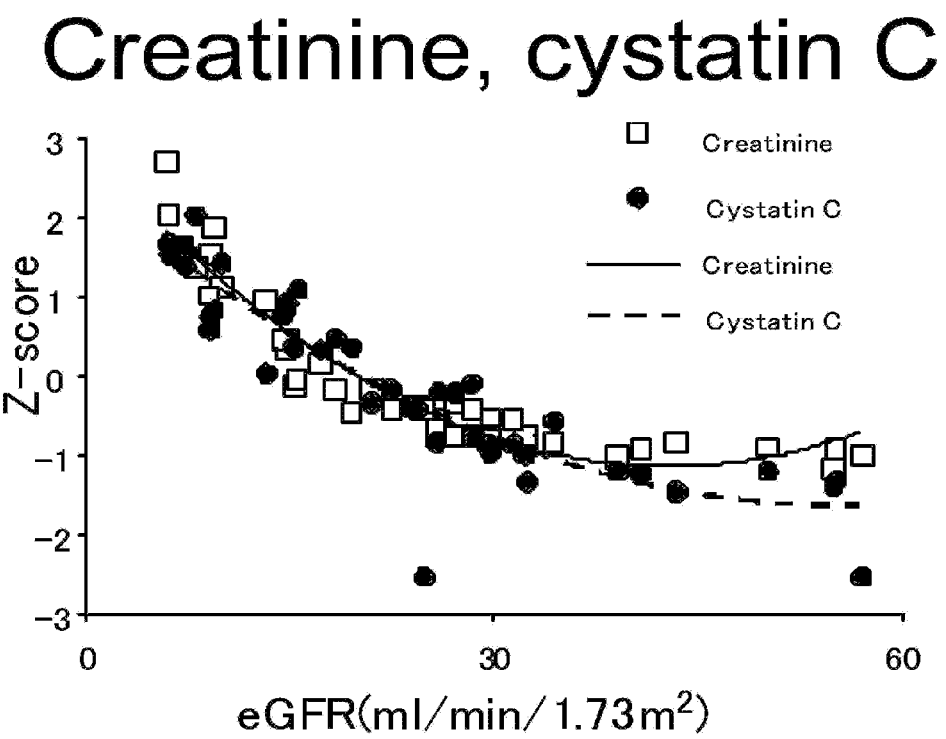
FIG. 68 is a graph showing the results of the comparison of the correlation with eGFR between the present marker substance for an early stage renal disease and cystatin C.
Figure 69:
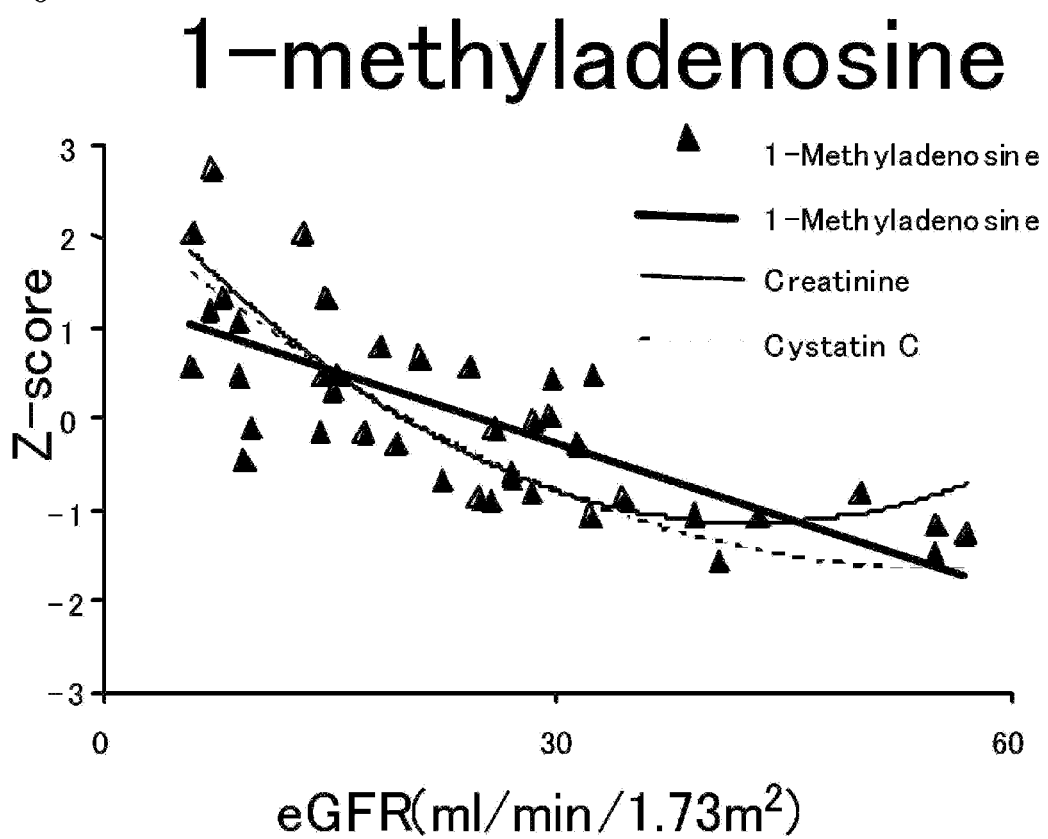
FIG. 69 is a graph showing the results of the comparison of the correlation with eGFR between the present marker substance for an early stage renal disease and 1-methyladenosine.
Figure 70:
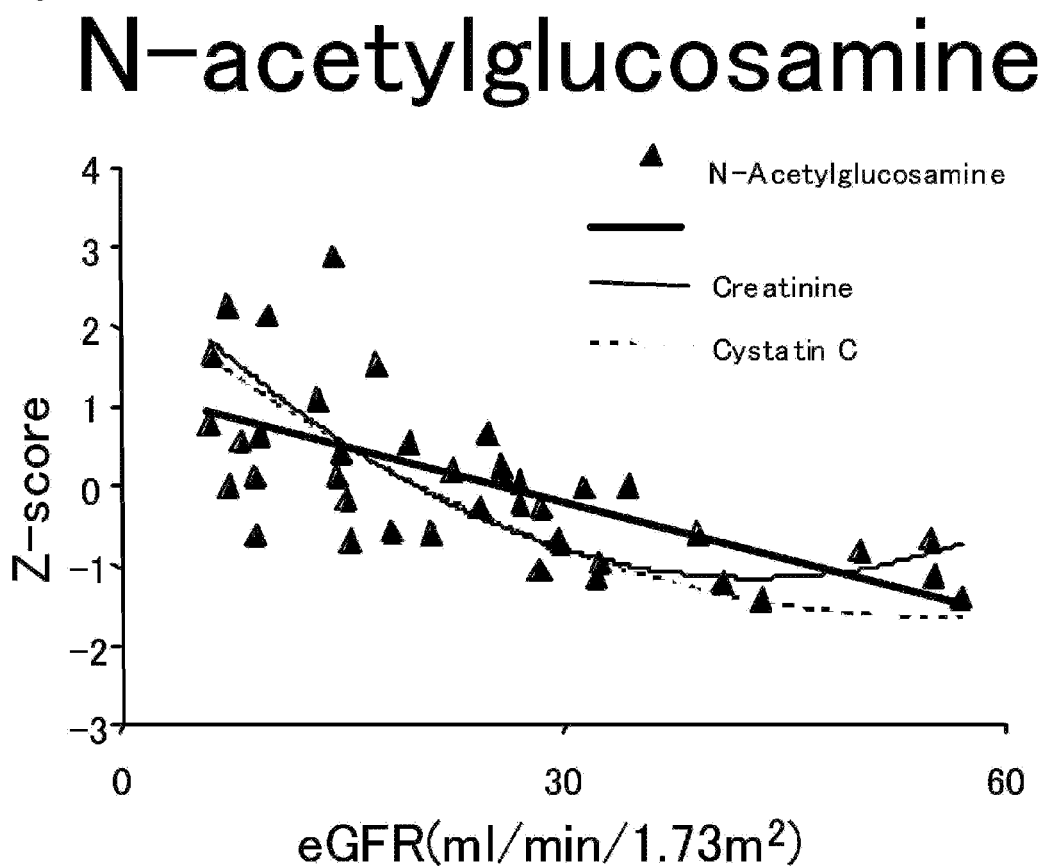
FIG. 70 is a graph showing the results of the comparison of the correlation with eGFR between the present marker substance for an early stage renal disease and N-acetylglucosamine.
Figure 71:
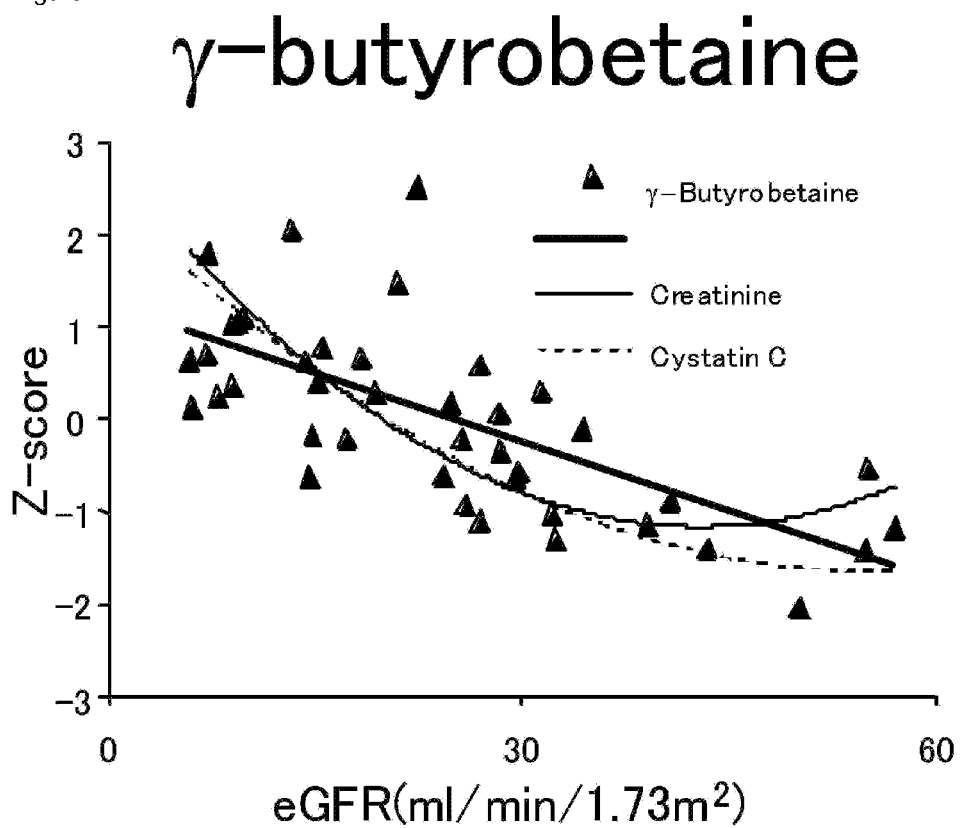
FIG. 71 is a graph showing the results of the comparison of the correlation with eGFR between the present marker substance for an early stage renal disease and γ-butyrobetaine.
Figure 72:
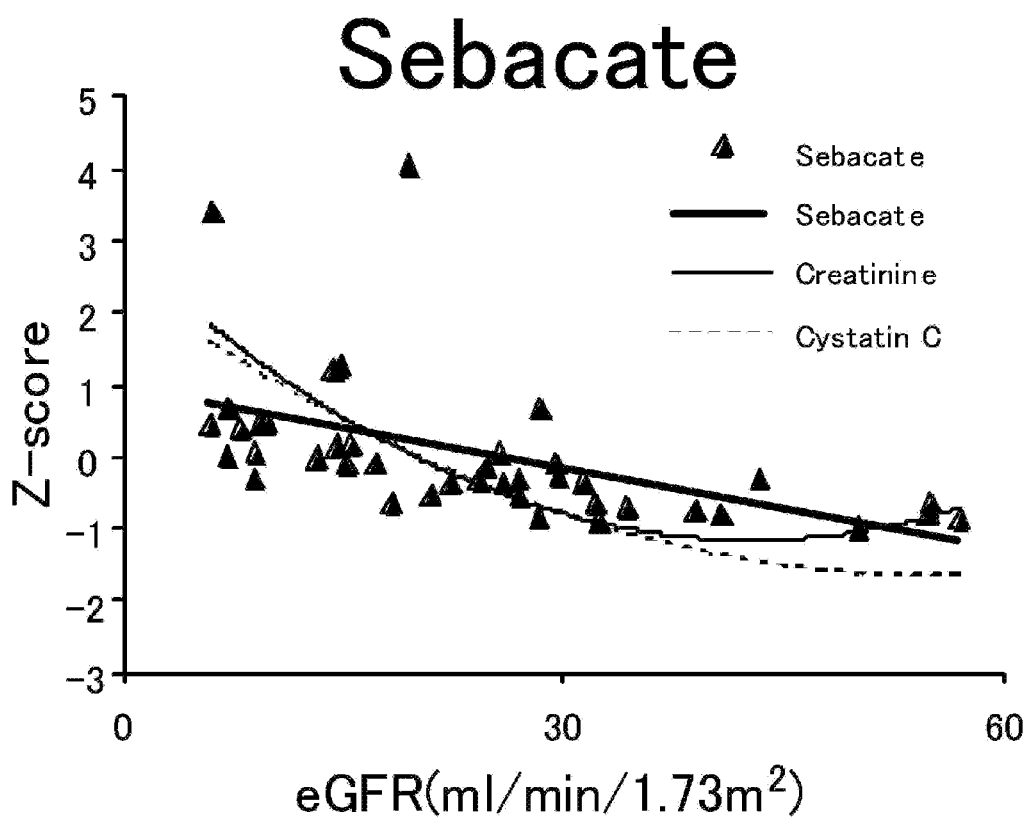
FIG. 72 is a graph showing the results of the comparison of the correlation with eGFR between the present marker substance for an early stage renal disease and sebacate.
Figure 73:
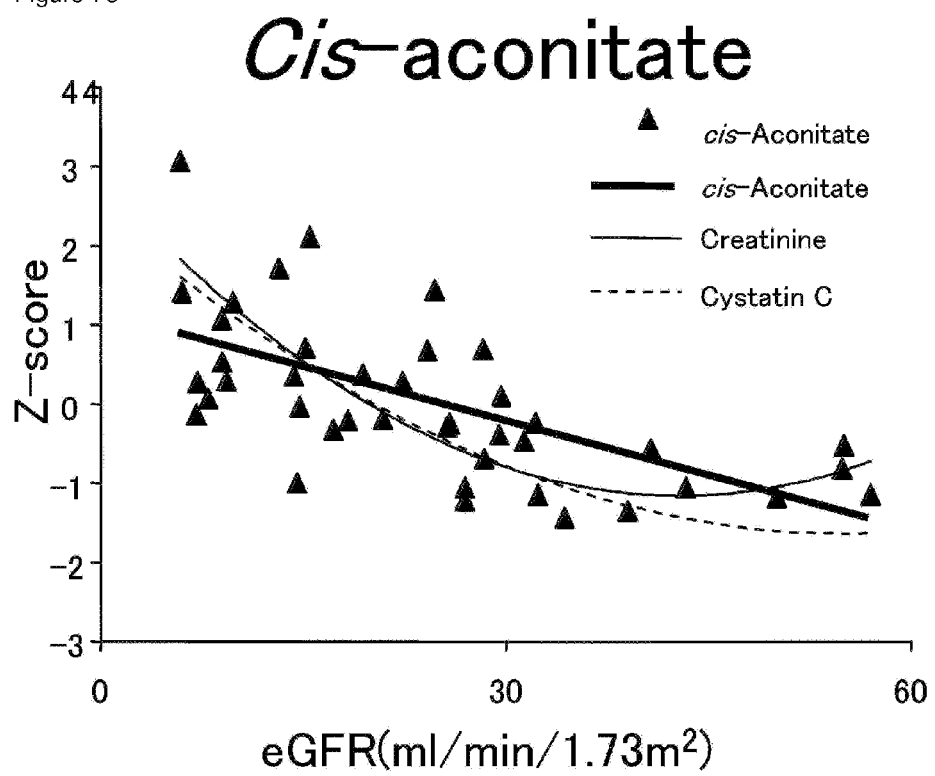
FIG. 73 is a graph showing the results of the comparison of the correlation with eGFR between the present marker substance for an early stage renal disease and cis-aconitate.
Figure 74:
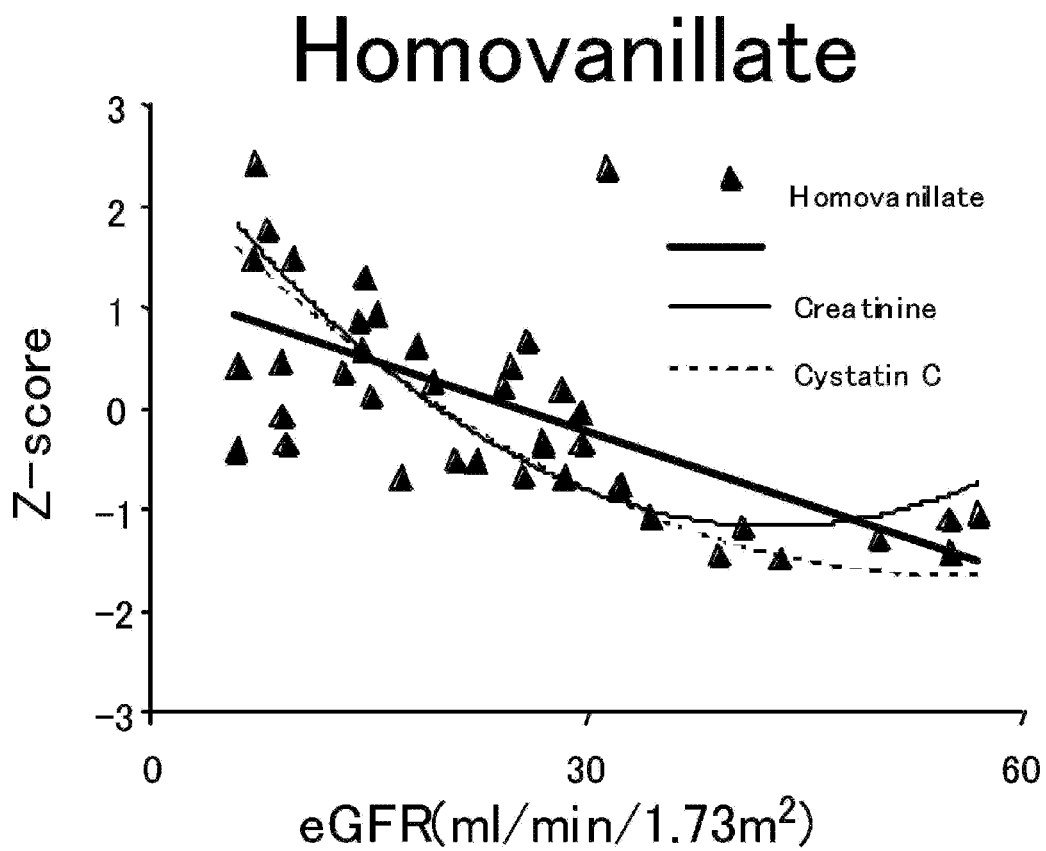
FIG. 74 is a graph showing the results of the comparison of the correlation with eGFR between the present marker substance for an early stage renal disease and homovanillate.
Figure 75:
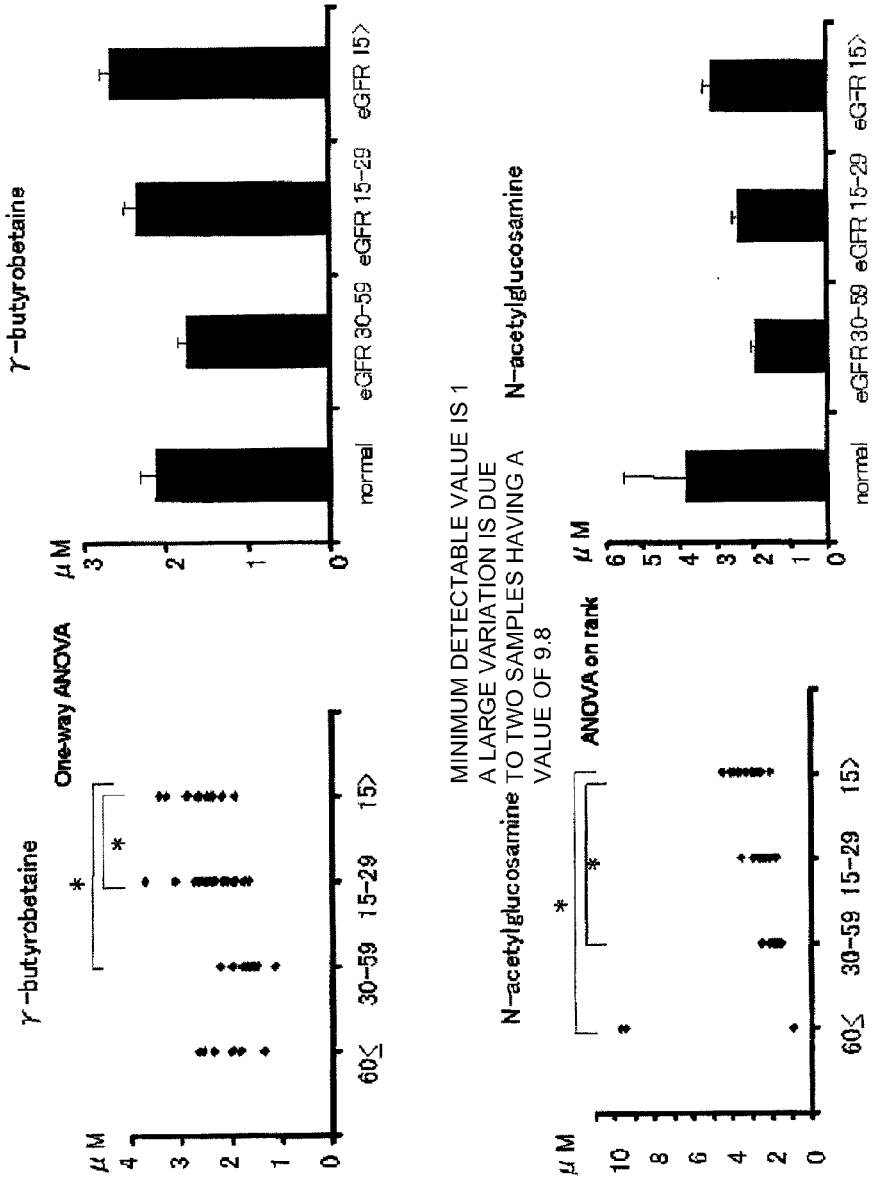
FIG. 75 is a set of diagrams showing the concentrations of the present marker substances for an early stage renal disease in a plasma sample (γ-butyrobetaine and N-acetylglucosamine) per group according to the eGFR level.
Figure 76:
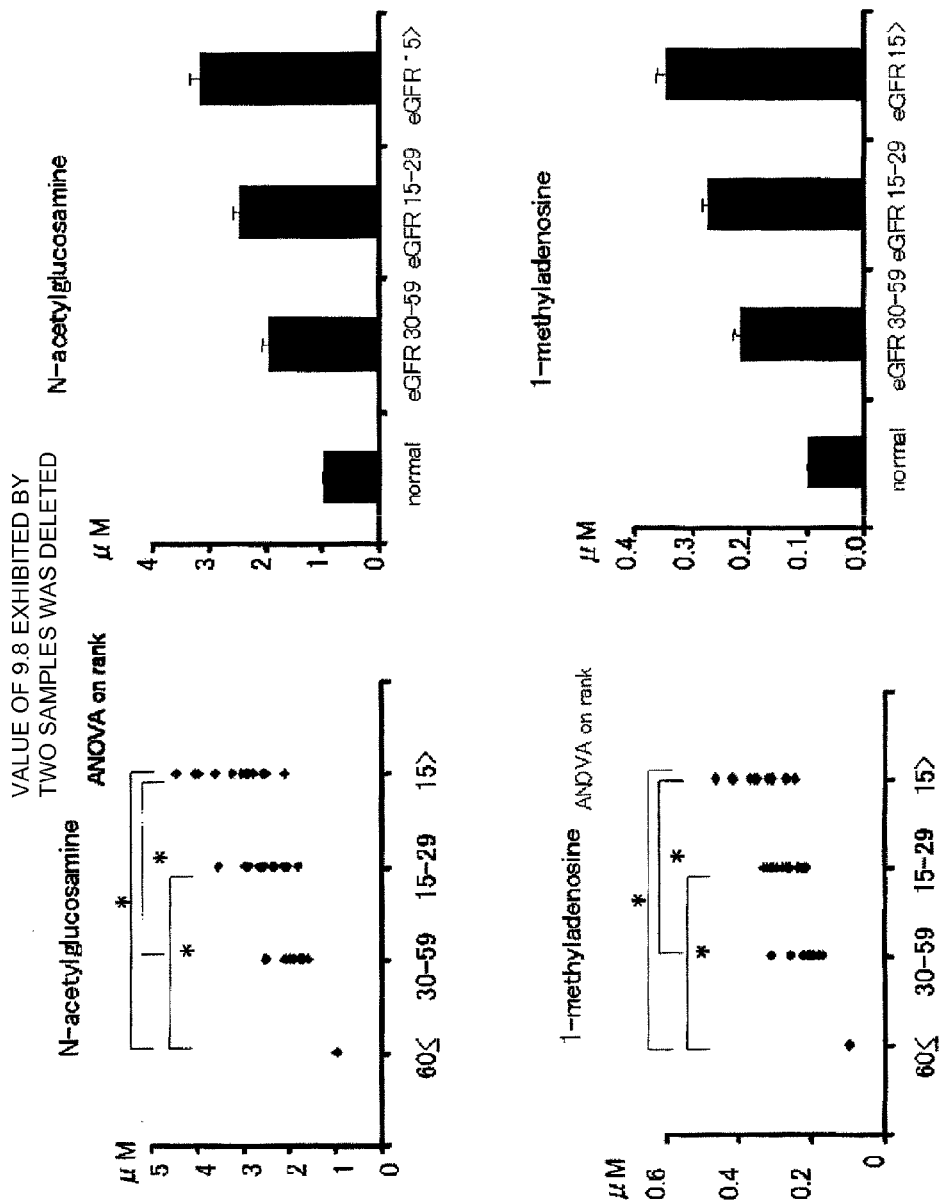
FIG. 76 is a set of diagrams showing the concentrations of the present marker substances for an early stage renal disease in a plasma sample (N-acetylglucosamine and 1-methyladenosine) per group according to the eGFR level.
Figure 77:
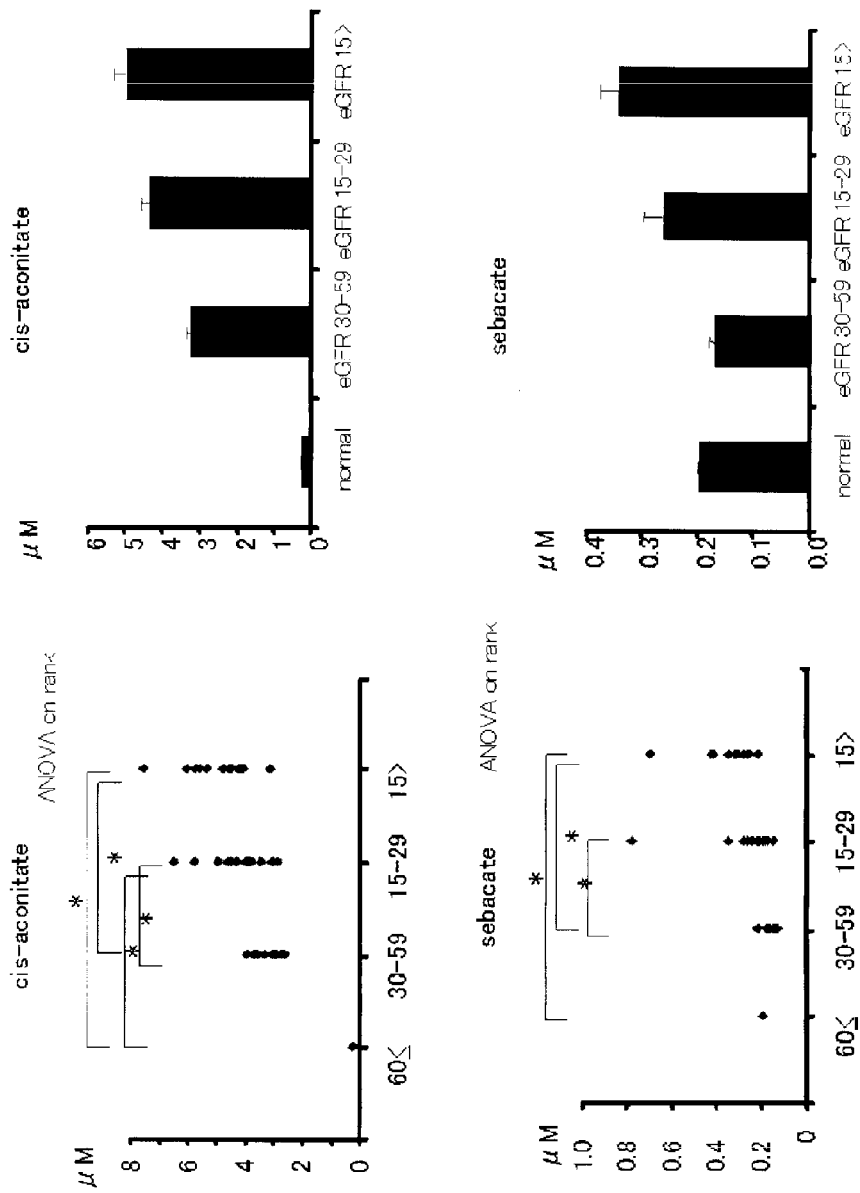
FIG. 77 shows diagrams of the concentrations of the present marker substances for an early stage renal disease in a plasma sample (cis-aconitate and sebacate) per group according to the eGFR level.
Figure 78:
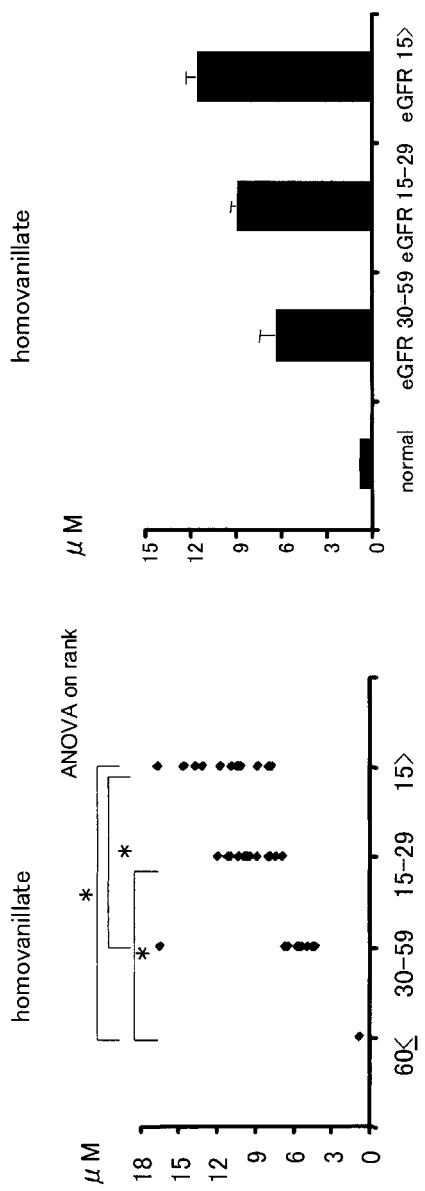
FIG. 78 is a set of diagrams showing the concentrations of the present marker substance for an early stage renal disease in a plasma sample (homovanillate) per group according to the eGFR level.

Among the currently used, publicly known renal disease marker substances, the correlation equation between creatinine and eGFR was already shown to approximate to a quadratic equation in FIG. 19. In view of this, the correlation equation between cystatin C, which is now said to be an alternative renal disease marker substance to creatinine, with eGFR was also examined. Specifically, cystatin C in the plasma samples obtained from all of the patients with a renal disease collected in Example 1 was analyzed by CE-MS similarly to Example 2. Subsequently, based on the analytical results thus obtained, the correlation between eGFR and cystatin C was examined. The results thus obtained are shown in FIG. 68. As is understood from these results, it was similarly observed that while the blood concentration of cystatin C gradually increased with a reduction in eGFR, particularly in terminal renal disease, it exhibited an abruptly ascending curve which rather resembled a quadratic curve. Therefore, unlike the present marker substance for an early stage renal disease, not only creatinine but also cystatin C was shown to be unsuitable for detection of an early stage renal disease. Also, for reference, six Figures comparing the present marker substance for an early stage renal diseases and the publicly known renal disease marker substances (creatinine and cystatin C) with respect to the correlation with eGFR are shown in FIGS. 69 to 74. As is shown in these Figures, the present marker substance for an early stage renal disease exhibited more sensitive concentration changes in response to a drop in eGFR than did creatinine and cystatin C. From the above results, it was shown that the present marker substance for an early stage renal disease is particularly excellent for determination of an early stage renal disease compared to conventional renal disease marker substances.

Example 5

Comparison of the Plasma Concentration of the Renal Disease Marker Substance in Patients with a Renal Disease with that in Healthy Individuals The plasma concentration of the renal disease marker substance and eGFR in patients with a renal disease were analyzed in the aforementioned Examples 2 and 3. In order to compare the analytical results thus obtained with those values in healthy individuals, the plasma concentration of the renal disease marker substance in healthy individuals was measured.

Firstly, plasma samples for CE-MS analysis as described above were obtained from 18 healthy individuals. The background of these individuals was as follows; an average age was 55, and all of them were males. As a result of calculation of eGFR of these healthy individuals by the aforementioned estimation formula recommended by Japanese Society of Nephrology, all the healthy individuals were classified as having a value equal to or greater than 60 ml/min/1.73 m$^2$, which is the standard for normality.

The plasma samples collected from these healthy individuals were analyzed by CE-MS by a similar method to Example 2 described above, and the concentrations of a total of six substances, namely γ-butyrobetaine, N-acetylglucosamine, 1-methyladenosine, cis-aconitate, sebacate, and homovanillate were measured. Subsequently, an average value of the concentration of each of the above substances was calculated. Also, among the substances whose concentrations in the plasma samples of the patients with a renal disease were measured in the aforementioned Example 2, an average value of the concentration of each of the aforementioned six substances was calculated for each of the three groups classified according to the eGFR value of the patients with a renal disease (eGFR 30 to 59, eGFR 15 to 29, and eGFR 15>). FIGS. 75 to 78 show the results of each of the aforementioned six substances for each of a group of healthy individual (nomal), a group of patients with a renal disease with eGFR of 30 to 59 (eGFR 30 to 59), a group of patients with a renal disease with eGFR of 15 to 29 (eGFR 15 to 29), and a group of patients with a renal disease with eGFR of 15 or less (eGFR 15>). It is to be noted that, in the lower panels of FIG. 75, because two of the healthy individuals had extremely isolated N-acetylglucosamine concentration values from the rest of them, the N-acetylglucosamine concentration of these two individuals were excluded as abnormal values. The results thus obtained are shown in the upper panels of FIG. 76. Also, in the panels on the left of FIGS. 75 to 78, the measured concentrations are individually plotted as dots, and the panels on the right show bar graphs, where each bar represents the average of each group.

As is understood from the results shown in FIGS. 75 to 78, among the six kinds of substances, a tendency was observed that the substance concentration of 1-methyladenosine, cis-aconitate, and homovanillate increased with a reduction in eGFR, and even the concentrations of these substances in a group with slightly reduced eGFR (eGFR 30 to 59) were significantly different from those in healthy individuals. Among them, cis-aconitate and homovanillate, of which particularly cis-aconitate was found to exist at a very low concentration in healthy individuals (FIGS. 77 and 78), and thus was shown to be a particularly excellent renal disease marker.

INDUSTRIAL APPLICABILITY

The present invention can be preferably utilized in the field of determination of a renal disease and the field of screening for a prophylactic/therapeutic agent for a renal disease.

The invention claimed is:

1. A method for diagnosing and treating a renal disease in a patient, comprising the steps of:
   having a test performed for quantifying cis-aconitate present in a test blood sample from the patient, wherein the patient is identified as having the renal disease when a concentration of cis-aconitate present in the test blood sample is higher than that of a control; and
   administering treatment to the diagnosed patient to improve renal function of the diagnosed patient.

2. The method for diagnosing and treating a renal disease in a patient according to claim 1, further comprising the step of: having the result of quantification of cis-aconitate present in the test blood sample compared with that of a control to evaluate a degree of symptoms of the renal disease of the patient.

3. The method for diagnosing and treating renal disease in a patient according to claim 2, wherein the degree of severity of symptoms of a renal disease of the patient is evaluated to be equivalent to a degree by which a concentration of cis-aconitate present in the test blood sample exceeds a control.

4. The method for diagnosing and treating a renal disease in a patient according to any one of claims 1 to 3, wherein the renal disease is renal failure.

5. A method for diagnosing and treating a renal disease in a patient according to any one of claims 1 to 3, wherein the renal disease is early stage renal disease.

6. The method for diagnosing and treating early stage a renal disease in a patient according to claim 5, wherein the early stage renal disease is early stage renal failure.

* * * * *